United States Patent [19]

von Sprecher et al.

[11] Patent Number: 4,939,160
[45] Date of Patent: Jul. 3, 1990

[54] HYDROPYRIDINE DERIVATIVES

[75] Inventors: Georg von Sprecher, Allschwil; Wolfgang Fröstl; Armin Züst, both of Basel, all of Switzerland

[73] Assignee: Ciba-Geigy Corporation, Ardsley, N.Y.

[21] Appl. No.: 281,596

[22] Filed: Dec. 9, 1988

Related U.S. Application Data

[60] Division of Ser. No. 228,849, Aug. 3, 1988, Pat. No. 4,833,169, which is a continuation of Ser. No. 899,132, Aug. 21, 1986, abandoned.

[30] Foreign Application Priority Data

Aug. 27, 1985 [CH] Switzerland ............... 3669/85
Jun. 26, 1986 [CH] Switzerland ............... 2586/86

[51] Int. Cl.$^5$ ............... A61K 31/44; A61K 31/445; C07D 211/74; C07D 211/40
[52] U.S. Cl. ............... 514/319; 546/205; 546/206; 546/268; 546/193; 546/261; 546/262; 546/263; 546/318; 546/298; 514/336; 514/318; 514/332; 514/335; 514/350
[58] Field of Search ............... 546/205, 206, 261, 268, 546/262, 263, 326, 318, 193, 298; 514/319, 336, 350, 318

[56] References Cited

U.S. PATENT DOCUMENTS

| | | | |
|---|---|---|---|
| 3,408,391 | 10/1968 | Skorcz ............... | 260/518 |
| 3,513,244 | 5/1970 | Gittos et al. ............... | 424/320 |
| 3,534,055 | 10/1970 | Gittos et al. ............... | 260/295 |
| 3,622,614 | 11/1971 | Jenny ............... | 260/465 |
| 3,629,463 | 12/1971 | Gittos et al. ............... | 424/330 |
| 4,238,488 | 12/1980 | Howe et al. ............... | 424/248.55 |
| 4,383,999 | 5/1983 | Bondinell et al. ............... | 424/266 |
| 4,410,519 | 10/1983 | Seiler et al. ............... | 424/226 |
| 4,446,141 | 5/1984 | Nakamizo et al. ............... | 424/267 |
| 4,629,727 | 12/1986 | Kozlik et al. ............... | 514/237.8 |
| 4,647,559 | 3/1987 | Kuhla et al. ............... | 546/206 |

FOREIGN PATENT DOCUMENTS

| | | |
|---|---|---|
| 115409 | 8/1984 | European Pat. Off. . |
| 1094255 | 12/1960 | Fed. Rep. of Germany . |
| 2252945 | 5/1974 | Fed. Rep. of Germany . |
| 2319330 | of 1977 | France . |
| 6408887 | of 1965 | Netherlands . |
| 491615 | of 1976 | U.S.S.R. . |
| 932487 | 7/1963 | United Kingdom . |
| 1037014 | 7/1966 | United Kingdom . |
| 1143430 | 2/1969 | United Kingdom . |
| 1187017 | 4/1970 | United Kingdom . |

OTHER PUBLICATIONS

CA97:109663x, Stuches on the Amine Exchange Reactions in C-Mannich Bases, Kulkarni et al., Irclian Chem. Soc., 1982.
J. Med. Chem., vol. 25, pp. 1358-1363 (1982).
Derwent Abstract 84-196786/32 of European 115 409A (1984).
Derwent Abstract 85-035839/06 of Japanese 59231-05-2-A.
Derwent Abstract 15622y/09 of Japanese 52007946 (1977).
Derwent Abstract 4286y/08 of S.U. 491615 (1976).
Dictionary of Organic Compounds, 5th Ed. (1982).
Derwent Abstract of French Patent No. 2,319,330 (1975).

*Primary Examiner*—Mary C. Lee
*Assistant Examiner*—Catherine S. Scalzo
*Attorney, Agent, or Firm*—JoAnn Villamizar

[57] ABSTRACT

Hydropyridine derivatives of the formula

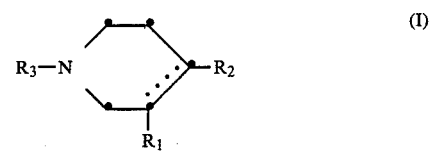

in which $R_1$ represents carboxy, lower alkoxycarbonyl, carbamoyl, N-lower alkylcarbamoyl or N,N-di-lower alkylcarbamoyl, $R_2$ represents hydrogen, an optionally etherified or acylated hydroxy group or an optionally acylated amino group, and $R_3$ represents a radical of the formula R- (Ia), R-alk$_1$- (Ib) or R'=alk$_2$- (Ic) in which R represents a benzocycloalkenyl radical having a total of from 8 to 12 ring carbon atoms which is bonded via a saturated carbon atom and which is unsubstituted or is mono- or poly-substituted in the benzo moiety by hydroxy, lower alkoxy, lower alkanoyloxy, halogen, lower alkyl and/or by trifluoromethyl, and/or substituted in the α-position by lower alkyl, and R' represents a benzocycloalkylidene radical having a total of from 8 to 12 ring carbon atoms which is unsubstituted or is mono- or poly-substituted in the benzo moiety by hydroxy, lower alkoxy, lower alkanoyloxy, halogen, lower alkyl and/or by trifluoromethyl, and alk$_1$ represents lower alkylene or lower alkylidene and alk$_2$ represents lower alkyl-ω-ylidene, wherein the dotted line is intended to show that there may be a single bond or especially a double bond, and 3-aminopropionic acid compounds of the formula $R_3$—NH—CH$_2$CH$_2$—R$_1$ (IVc) in which $R_1$ and $R_3$ have the meanings given above, and their pharmaceutically acceptable salts, have nootropic properties and can be used as nootropic active ingredients in medicaments. They are manufactured by methods known per se.

13 Claims, No Drawings

HYDROPYRIDINE DERIVATIVES

This is a divisional of application Ser. No. 228,849 filed on Aug. 3, 1988, issued 5-23-89 as U.S. Pat. No. 4,833,169 which was an FWC of 6/899,132, filed 8/21/86, now abandoned.

The invention relates to novel hydropyridine derivatives of the formula

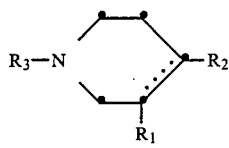
(I)

in which $R_1$ represents carboxy, lower alkoxycarbonyl, carbamoyl, N-lower alkylcarbamoyl or N,N-di-lower alkylcarbamoyl, $R_2$ represents hydrogen, an optionally etherified or acylated hydroxy group or an optionally acylated amino group, and $R_3$ represents a radical of the formula R- (Ia), R-alk$_1$- (Ib) or R'=alk$_2$- (Ic) in which R represents a benzocycloalkenyl radical having a total of from 8 to 12 ring carbon atoms which is bonded via a saturated carbon atom and which is unsubstituted or is mono- or poly-substituted in the benzo moiety by hydroxy, lower alkoxy, lower alkanoyloxy, halogen, lower alkyl and/or by trifluoromethyl, and/or substituted in the α-position by lower alkyl, and R' represents a benzocycloalkylidene radical having a total of from 8 to 12 ring carbon atoms which is unsubstituted or is mono-or poly-substituted in the benzo moiety by hydroxy, lower alkoxy, lower alkanoyloxy, halogen, lower alkyl and/or by trifluoromethyl, and alk$_1$ represents lower alkylene or lower alkylidene and alk$_2$ represents lower alkyl-ω-ylidene, wherein the dotted line is intended to show that there may be a single bond or especially a double bond, their tautomers and/or salts, to the use of these compounds, to processes for their manufacture and to pharmaceutical compositions containing a compound of the formula I or a tautomer and/or pharmaceutically acceptable salt thereof.

The radical R or R' may have one or more, for example one or two or three identical or different substituents from among those mentioned.

Radicals R according to the definition given above are, for example, benzocyclobutenyl radicals, for example benzocyclobuten-1-yl, indanyl radicals, for example indan-1-yl or, secondly, indan-2-yl radicals, or 1,2,3,4-tetrahydronaphthyl radicals, for example 1,2,3,4-tetrahydronaphth-1-yl or, secondly, 1,2,3,4-tetrahydronaphth-2-yl.

Radicals R' according to the definition given above are, for example, benzocyclobutenylidene radicals, for example benzocyclobuten-1-ylidene.

The invention relates, for example, to novel hydropyridine derivatives of the formula I in which $R_3$ represents a group Ia or Ib, R represents a benzocyclobuten-1-yl radical which is unsubstituted or is mono- or poly-substituted in the benzo moiety by hydroxy, lower alkoxy, lower alkanoyloxy, halogen, lower alkyl and/or by trifluoromethyl, and/or substituted in the α-position by lower alkyl, $R_1$ represents carboxy, lower alkoxycarbonyl, carbamoyl, N-lower alkylcarbamoyl or N,N-di-lower alkylcarbamoyl, $R_2$ represents hydrogen, an optionally etherified or acylated hydroxy group or an optionally acylated amino group, and alk$_1$ represents lower alkylene or lower alkylidene, their tautomers and salts, to the use of these compounds, to processes for their manufacture and to pharmaceutical compositions containing a corresponding compound of the formula I or a tautomer and/or pharmaceutically acceptable salt thereof.

Etherified hydroxy $R_2$ is, for example, lower alkoxy or optionally substituted phenyl-lower alkoxy.

Acyl in acylated hydroxy or amino $R_2$ is, for example, acyl derived from an organic carboxylic or sulphonic acid or from a semiester of carbonic acid.

Acyl derived from organic carboxylic acids is, for example, the radical of an aliphatic or monocyclic aromatic carboxylic acid, such as lower alkanoyl or optionally substituted benzoyl, and also pyridoyl.

Acyl derived from organic sulphonic acids is, for example, lower alkanesulphonyl.

In acyl derived from semiesters of carbonic acid, the second hydroxy group is esterified, for example, by an aliphatic or arylaliphatic, such as phenylaliphatic, alcohol. There may be mentioned as acyl groups derived from semiesters of carbonic acid, for example, lower alkoxycarbonyl and optionally substituted phenyl-lower alkoxycarbonyl.

Tautomeric forms of compounds of the formula I exist, for example, when $R_2$ represents hydroxy or amino and the dotted line is intended to show that there is a double bond. That is to say, the enols or enamines of the formula I are in equilibrium with the corresponding keto or ketimine tautomers of the formula

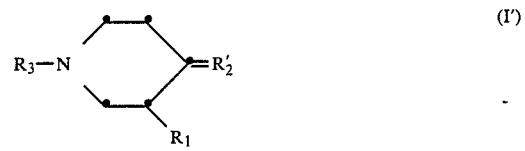
(I')

in which $R_2'$ represents oxo or imino. Representatives of both tautomeric forms can be isolated.

The compounds according to the invention may also be in the form of stereoisomers. Since the compounds of the formula I have at least one chiral carbon atom (for example the α-carbon atom of the radical R or R' if substituted by lower alkyl, or the carbon atom in the 3-position of a 4-unsubstituted piperidine radical), they may, for example, be in the form of pure enantiomers or enantiomeric mixtures, such as racemates, and, if at least one further chiral centre is present (for example the carbon atom in the 4-position of a 4-substituted piperidine radical), in the form of diastereoisomers or diastereoisomeric mixtures. Thus, for example, with regard to $R_1$ and $R_2$, geometrical isomers, such as cis-, i.e. 3S,4S- and 3R,4R-, and trans-, i.e. 3S,4R- and 3R,4S-, isomers may also be formed if $R_2$ is other than hydrogen.

Salts of compounds of the formula I or the tautomers thereof are especially corresponding acid addition salts, preferably pharmaceutically acceptable acid addition salts. These are formed, for example, with strong inorganic acids, such as mineral acids, for example sulphuric acid, a phosphoric acid or a hydrohalic acid, with strong organic carboxylic acids, such as lower alkanecarboxylic acids, for example acetic acid, optionally unsaturated dicarboxylic acids, for example malonic, maleic or fumaric acid, or hydroxycarboxylic acids, for example tartaric or citric acid, or with sulphonic acids, such as lower alkane- or optionally substituted benzene-sulphonic acids, for example methane- or p-toluene-sulphonic acid. If $R_1$ represents, for example, carboxy, corresponding compounds may form salts with bases. Suitable salts with bases are, for example, corresponding alkali metal salts or alkaline earth metal salts, for example sodium, potassium or magnesium salts, pharmaceutically acceptable transition metal salts, such as zinc or copper salts, or salts with ammonia or organic amines, such as cyclic amines, mono-, di- or tri-lower alkylamines, hydroxy-lower alkylamines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. As mono-lower alkylamines there come into consideration, for example, ethyl- or tert.-butyl-amine, as di-lower alkylamines, for example, diethyl- or diisopropyl-amine, and as tri-lower alkylamines, for example, trimethyl- or triethyl-amine. Corresponding hydroxy-lower alkylamines are, for example, mono-, di- and tri-ethanolamine, and hydroxy-lower alkyl-lower alkylamines are, for example, N,N-dimethylamino- or N,N-diethylaminoethanol, and as polyhydroxy-lower alkylamine there comes into consideration, for example, glucosamine.

Also included are salts that are unsuitable for pharmaceutical uses, since these may be used, for example, for the isolation or purification of free compounds according to the invention and their pharmaceutically acceptable salts.

Hereinbefore and hereinafter there is to be understood by radicals or compounds referred to as "lower", unless defined otherwise, especially radicals or compounds that contain up to and including 7, especially up to and including 4, carbon atoms.

Lower alkoxy is, for example, methoxy, ethoxy, n-propoxy, isopropoxy, n-butoxy, isobutoxy and tert.-butoxy.

Lower alkyl is, for example, methyl, ethyl, n-propyl, isopropyl, n-butyl, isobutyl, sec.-butyl or tert.-butyl and also includes corresponding pentyl, hexyl and heptyl radicals.

Lower alkylene $alk_1$ bridges the two ring systems especially by from 1 up to and including 3 carbon atoms and has especially from 1 up to and including 4, above all 2 up to and including 3, carbon atoms and is, for example, straight-chained, such as methylene, ethylene or 1,3-propylene, or branched, such as 1,2-propylene, 1,2- or 1,3-(2-methyl)propylene or 1,2- or 1,3-butylene.

Lower alkylidene $alk_1$ bridges the two ring systems by 1 carbon atom and has especially from 1 up to and including 4, above all from 1 up to and including 3, carbon atoms and is, for example, methylene, ethylidene, 1,1- or 2,2-propylidene or 1,1- or 2,2-butylidene.

Lower alkyl-ω-ylidene $alk_2$ bridges the two ring systems especially by 2 or 3 carbon atoms and has especially from 2 up to and including 4, above all 2 or 3, carbon atoms and is, for example, ethyl-2-ylidene or propyl-3-ylidene.

Lower alkanoyl is, for example, acetyl, propionyl, butyryl, isobutyryl or pivaloyl.

Lower alkanesulphonyl is, for example, methane- or ethane-sulphonyl, and phenyl-lower alkoxy is, for example, α-phenyl-lower alkoxy having up to and including 4 alkyl carbon atoms, especially benzyloxy, which is optionally substituted by lower alkyl, lower alkoxy and/or by halogen.

Halogen is especially halogen having an atomic number of up to and including 35, such as fluorine, chlorine and bromine, and also includes iodine.

The compounds of the formula I, their tautomers and their pharmaceutically acceptable salts have, for example, valuable pharmacological, especially nootropic, properties. For example, in the case of mice, in the Two-Compartment Passive Avoidance Test model according to Mondadori and Classen, Acta Neurol. Scand. 69, Suppl. 99, pages 125–129 (1984), at dosages of approximately 0.1 mg/kg and above i.p. and p.o. they bring about a reduction in the amnesic effect of a cerebral electric shock.

The compounds according to the invention also exhibit a considerable memory-improving action which is to be detected in mice in the Step-down Passive Avoidance Test according to Mondadori and Waser, Psychopharmacol. 63. pages 297–300 (1979) at a dosage of approximately 0.1 mg/kg and above i.p. and p.o..

Accordingly, the compounds of the formula I or the tautomers thereof and their pharmaceutically acceptable salts can be used as pharmaceuticals, for example nootropics, for example for the therapeutic and prophylactic treatment of memory disorders. The invention therefore relates also to the use of compounds of the formula I, their tautomers and their pharmaceutically acceptable salts for the manufacture of medicaments, especially nootropics, for the treatment of memory disorders. The commercial formulation of the active substances may also be included.

The invention relates especially to compounds of the formula I in which R and R' each represents a benzocyclobuten-1-yl radical, benzocyclobuten-1-ylidene radical, indan-1-yl or indan-2-yl radical or 1,2,3,4-tetrahydronaphth-1-yl or 1,2,3,4-tetrahydronapth-2-yl radical each of which is unsubstituted or is mono- or poly-substituted, for example di- or tri-substituted, in the benzo moiety by hydroxy, lower alkoxy, lower alkanoyloxy and/or by halogen, and/or substituted in the α-position by lower alkyl, $R_1$ represents carboxy, lower alkoxycarbonyl or carbamoyl, $R_2$ represents hydrogen, hydroxy, lower alkoxy, lower alkanoyloxy, lower alkanesulphonyloxy, phenyl-lower alkoxy optionally substituted in the phenyl moiety by lower alkyl, lower alkoxy and/or by halogen, or amino, $alk_1$ represents lower alkylene or lower alkylidene which in each case connects the two ring systems by 1 or 2, respectively, up to and including 3 carbon atoms, and $alk_2$ represents lower alkyl-ω-ylidene which connects the two ring systems by 2 or 3 carbon atoms, and their tautomers and/or salts.

The invention relates especially, for example, to compounds of the formula I in which $R_3$ represents a group of the formula Ib, R represents a benzocyclobuten-1-yl radical which is unsubstituted or is mono- or poly-substituted, for example di- or tri-substituted, in the benzo moiety by hydroxy, lower alkoxy, lower alkanoyloxy and/or by halogen, and/or substituted in the 1-position by lower alkyl, $R_1$ represents carboxy, lower alkoxycarbonyl or carbamoyl, $R_2$ represents hydrogen, hydroxy, lower alkoxy, lower alkanoyloxy or amino, $alk_1$ represents lower alkylene or lower alkylidene which connects the two ring systems by 1 or 2, respectively, up to and including 3 carbon atoms, and their tautomers and/or salts.

The invention relates above all to compounds of the formula I in which $R_3$ represents a group Ia or Ib, R represents a benzocyclobuten-1-yl radical, indan-1-yl radical or, secondly, indan-2-yl radical or 1,2,3,4-tetrahydronaphth-1-yl radical each of which is unsubstituted or is mono-substituted in the benzo moiety by lower alkoxy having up to and including 4 carbon atoms, such as methoxy, lower alkyl having up to and including 4 carbon atoms, such as methyl, or by halogen having an atomic number of up to and including 35, such as chlorine, or di-substituted in the benzo moiety by lower alkyl having up to and including 4 carbon atoms, such as methyl, or by lower alkoxy having up to and including 4 carbon atoms, such as methoxy, and also by lower alkyl having up to and including 4 carbon atoms, such as methyl, $R_1$ represents lower alkoxycarbonyl, especially having from 2 up to and including 5 carbon atoms, such as ethoxycarbonyl, or carbamoyl, $R_2$ represents hydrogen or hydroxy, $alk_1$ represents lower alkylene which bridges the ring systems by from 1 up to and including 3 carbon atoms, especially having up to and including 3 carbon atoms, such as methylene, and the dotted line is intended to show that there may be a single bond or especially a double bond, and their tautomers and/or salts.

The invention relates above all, for example, to compounds of the formula I in which $R_3$ represents a group of the formula Ib, R represents a benzocyclobuten-1-yl radical which is unsubstituted or is substituted in the benzo moiety by lower alkoxy having up to and including 4 carbon atoms, such as methoxy, $R_1$ represents lower alkoxycarbonyl, especially having from 2 up to and including 5 carbon atoms, such as ethoxycarbonyl, or carbamoyl, $R_2$ represents hydrogen or hydroxy, $alk_1$ represents lower alkylene which bridges the ring systems by from 1 up to and including 3 carbon atoms, especially having up to and including 3 carbon atoms, such as methylene, and the dotted line is intended to show that there may be a single bond or especially a double bond, and their tautomers and/or salts.

The invention relates first and foremost to compounds of the formula I in which $R_3$ represents a group of the formula Ib, R represents a benzocyclobuten-1-yl radical which is unsubstituted or is monosubstituted in the benzo moiety, especially in the 5-position, by lower alkoxy having up to and including 4 carbon atoms, such as methoxy, $R_1$ represents lower alkoxycarbonyl having from 2 up to and including 5 carbon atoms, such as ethoxycarbonyl, $R_2$ represents hydroxy, $alk_1$ represents methylene or ethylene, and the dotted line is intended to show that there may be a single bond or especially a double bond, and their tautometers and/or salts.

The invention relates preferably to the novel compounds mentioned in the Examples and to processes for the manufacture thereof.

The present invention relates also to a process for the manufacture of compounds of the formula I, their tautomers and/or salts, for example characterised in that (a) a compound of the formula $$R_3-X_1 \quad (IIa),$$

or a salt thereof, in which $X_1$ represents hydroxy or reactive esterified hydroxy is reacted with a compound of the formula

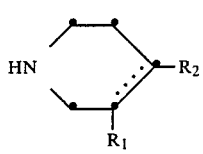
(IIb)

or with a tautomer or salt thereof, or (b) in a compound of the formula

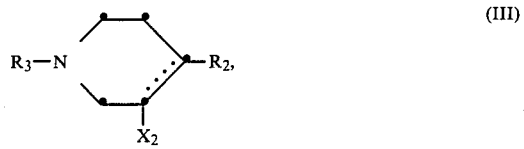
(III)

or in a tautomer or salt thereof, in which $X_2$ represents a radical that can be converted into $R_1$, $X_2$ is converted into $R_1$, or (c) for the manufacture of compounds of the formula I in which $R_2$ represents hydroxy or amino and in which $R_1$ represents especially lower alkoxycarbonyl, their tautomers and/or salts, a compound of the formula

(IV)

in which $Y_1$ represents a group of the formula $-CH=R_2'$, $C(Y_2)-R_2'$ or cyano and $R_2'$ represents oxo or imino, $Y_2$ representing a removable radical, or a salt thereof, is cyclised, or (d) for the manufacture of compounds of the formula I in which $R_2$ represents hydroxy or amino and the dotted line is intended to show that there is a double bond, and in which $R_1$ represents especially lower alkoxycarbonyl, their tautomers and/or salts, a compound of the formula

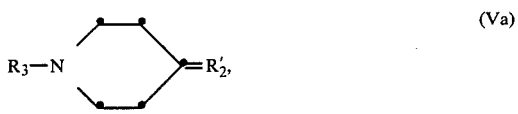
(Va)

or a tautomer or salt thereof, is reacted with a compound of the formula $$X_3-R_1 \quad (Vb)$$

in which $X_3$ represents halogen or lower alkoxy, or with a salt thereof, or (e) for the manufacture of compounds of the formula I in which $R_2$ is other than hydrogen, their tautomers and/or salts, in a compound of the formula

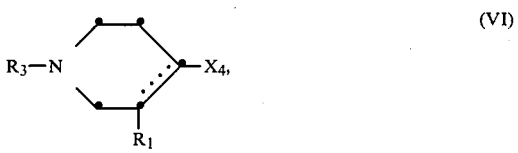
(VI)

or in a salt thereof, in which $X_4$ represents a radical that can be converted into $R_2$, $X_4$ is converted into $R_2$, or (f) especially for the manufacture of compounds of the formula I in which $R_2$ represents hydrogen, their tautomers and/or salts, in a compound of the formula

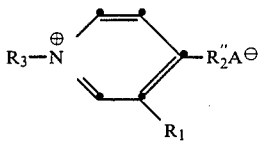

(VII)

in which $A^{\ominus}$ represents the anion of an acid and $R_2''$ represents hydrogen, also etherified, esterified or protected hydroxy or acylated or protected amino, the excess double bonds are reduced to single bonds and a protecting group which may be present is removed and, in each case if desired, a compound obtainable according to the process or in a different manner is converted into a different compound of the formula I, an isomeric mixture obtainable according to the process is separated into its components, an enantiomeric or diastereoisomeric mixture obtainable according to the process is split into the enantiomers or diastereoisomers, respectively, a free compound obtainable according to the process is converted into a salt and/or a salt obtainable according to the process is converted into the free compound or into a different salt.

The reactions described hereinbefore and hereinafter are carried out in a manner known per se, for example in the absence, or customarily in the presence, of a suitable solvent or diluent or a mixture thereof, the reactions being carried out, as necessary, while cooling, at room temperature or while heating, for example in a temperature range of from approximately −10° to the boiling temperature of the reaction medium, preferably at from approximately 20° to approximately 150° C., and, if necessary, in a closed vessel, under pressure, in an inert gas atmosphere and/or under anhydrous conditions.

Starting materials having basic centres may, for example, be in the form of acid addition salts, for example with the acids listed hereinbefore, whilst starting compounds having acid groups may form salts with bases, for example of the kind mentioned hereinbefore. Starting compounds may also be in the form of tautomers, especially in the case of compounds of the formula IIb when $R_2$ represents hydroxy and the dotted line is intended to show that there is a double bond.

Variant (a)

Reactive esterified hydroxy $X_1$ is especially hydroxy esterified by a strong inorganic acid or organic sulphonic acid, for example halogen, such as chlorine, bromine or iodine, sulphonyloxy, such as hydroxysulphonyloxy, halosulphonyloxy, for example fluorosulphonyloxy, lower alkanesulphonyloxy optionally substituted, for example, by halogen, for example methane- or trifluoromethane-sulphonyloxy, cycloalkanesulphonyloxy, for example cyclohexanesulphonyloxy, or benzenesulphonyloxy optionally substituted, for example, by lower alkyl or by halogen, for example p-bromophenyl- or p-toluene-sulphonyloxy.

The reaction is carried out especially in the presence of a condensation agent, such as a suitable base. Suitable bases are, for example, alkali metal hydroxides, hydrides, amides, alkoxides, carbonates, triphenylmethylides, di-lower alkylamides, amino-lower alkylamides or lower alkylsilylamides, naphthaleneamines, lower alkylamines, basic heterocycles, ammonium hydroxides and carbocyclic amines. There may be mentioned by way of example sodium hydroxide, hydride, amide or ethoxide, potassium tert.-butoxide or carbonate, lithium triphenylmethylide, lithium diisopropylamide, potassium 3-(aminopropyl)-amide or bis-(trimethylsilyl)-amide, dimethylaminonaphthalene, di- or tri-ethylamine, pyridine, benzyltrimethylammonium hydroxide, 1,5-diaza-bicyclo[4.3.0]non-5-ene (DBN) and 1,8-diazabicyclo[5.4.0]undec-7-ene (DBU).

The starting materials of the formula IIa are in some cases known. Novel compounds IIa in which $R_3$ represents a group Ib are obtained, for example, by reducing a corresponding ω-R-alkanecarboxylic acid with diborane or an ω-R-alkanecarboxylic acid ester with lithium aluminium hydride in each case to the corresponding alkanol (IIa; $X_1$ = hydroxy) and, if necessary, reactively esterifying the alcoholic hydroxy group, for example, using methanesulphonic acid chloride.

The starting materials of the formulae IIa and IIb are known or can be manufactured in a manner known per se.

Variant (b)

A radical $X_2$ that can be converted into $R_1$ is, for example, functionally modified carboxy other than $R_1$, such as cyano, anhydridised carboxy, optionally substituted amidino, optionally esterified or anhydridised carboximidoyl, esterified or amidated carboxy other than esterified or amidated carboxy $R_1$, tri-lower alkoxy- or tri-halo-methyl.

Anhydridised carboxy is, for example, carboxy anhydridised with a mineral acid, such as a hydrohalic acid, or with a carboxylic acid, such as an optionally substituted lower alkanoic or benzoic acid or a haloformic acid lower alkyl semiester. As examples there may be mentioned halocarbonyl, such as chlorocarbonyl, lower alkanoyloxycarbonyl, such as acetoxycarbonyl, or lower alkoxycarbonyloxycarbonyl, such as ethoxycarbonyloxycarbonyl.

Substituted amidino is, for example, amidino substituted by an aliphatic radical, for example lower alkyl, such as lower alkylamidino, for example ethylamidino.

Esterified or anhydridised carboximidoyl is to be understood as meaning, for example, alkoxy- or halocarbimidoyl, for example lower alkoxy-, such as ethoxy-, or chloro-carbimidoyl, respectively.

Tri-lower alkoxy- or tri-halo-methyl is, for example, trimethoxymethyl or trichloromethyl, respectively.

$X_2$ can be converted into $R_1$, for example, by solvolysis. Solvolysing agents are, for example, water, lower alkanols corresponding to the desired esterified carboxy, ammonia or amines corresponding to the desired amidated carboxy group $R_1$. The treatment with a corresponding solvolysing agent is optionally carried out in the presence of an acid or base. Suitable acids are, for example, inorganic or organic protonic acids, such as mineral acids, for example sulphuric acid or a hydrohalic acid, for example hydrochloric acid, sulphonic acids, for example lower alkane- or optionally substituted benzene-sulphonic acids, for example methane- or p-toluene-sulphonic acid, or carboxylic acids, for example lower alkanecarboxylic acids, for example acetic acid, whilst as bases there may be used, for example, those mentioned under Variant (a), especially sodium or potassium hydroxide.

In the solvolysis, anhydridised carboxy, optionally substituted amidino, optionally esterified or anhydridised carboximidoyl, esterified or amidated carboxy other than esterified or amidated carboxy $R_1$, tri-lower alkoxy- or trihalo-methyl is hydrolysed to carboxy, or cyano is hydrolysed to carbamoyl or carboxy. During this operation, lower alkanoyloxy radicals and/or etherified or acylated hydroxy groups that may be present at the ring R or acylated amino groups $R_2$ may be hydrolysed in the course of the hydrolysis to hydroxy or amino, respectively.

Cyano, anhydridised carboxy, or esterified or amidated carboxy other than esterified or amidated carboxy $R_1$ are alcoholysed, for example with a suitable lower alkanol, to esterified carboxy, and cyano and anhydridised carboxy are ammonolysed or aminolysed, for example with ammonia or with an amine corresponding to the amidated carboxy $R_1$, respectively.

The starting material of the formula III can be manufactured in a manner analogous to that described under Variant (a) by reacting a compound of the formula $R_3$—$X_1$ (IIa) with a compound of the formula

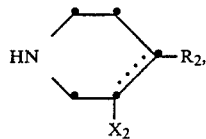
(IIIa)

a tautomer or salt thereof, in the presence of one of the mentioned bases.

Variant (c)

The cyclisation can be carried out, for example, analogously to the Dieckmann reaction, especially in the presence of one of the bases mentioned in Variant (a) and with subsequent working-up by means of hydrolysis.

In a preferred embodiment, for example a compound of the formula

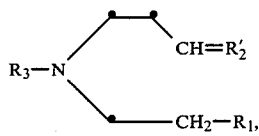
(IVa)

in which $R_2'$ represents oxo or imino, can be subjected to treatment with one of the mentioned bases, especially with an alkali metal lower alkoxide, for example with sodium methoxide or sodium ethoxide. During this treatment, the compound IVa cyclises to a compound of the formula I in which the dotted line indicates that there is no double bond and $R_2$ represents hydroxy or amino. Starting materials of the formula IVa are obtained, for example, by reacting a reactive benzocycloalkenyl(idene)alkanol ester of the formula $R_3$—$X_1$ (IIa)

in which $X_1$ is reactive esterified hydroxy, with a β-amino acid compound of the formula $H_2N$—$CH_2$—$CH_2$—$R_1$ (IVb) and reacting the resulting 3-aminopropionic acid derivative of the formula

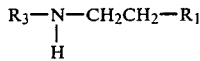
(IVc)

with acrolein or an optionally functionally modified aldehyde of the formula $Y_1$—$CH_2$—$CH_2$—$CH$=$R_2'$ (IVd; $Y_1$=reactive esterified hydroxy; $R_2'$=oxo or imino).

In another preferred embodiment of Variant (c), a compound of the formula IV in which $Y_1$ and $R_1$ represent lower alkoxycarbonyl is cyclised to the corresponding compound of the formula I in which the dotted line indicates that there is a double bond and $R_2$ represents hydroxy, or to the corresponding tautomer of the formula I in which $R_2'$ is oxo.

For the manufacture of the last-mentioned starting compounds of the formula IV, it is possible to use as starting materials, for example, compounds of the formula $R_3$—$NH_2$ (IVe), or the salts thereof, which are obtainable, for example, by reduction of the corresponding nitriles, and which are reacted with at least 2 moles of a compound of the formula $CH_2$=$CH$—$R_1$ (IVf).

Compounds IVc in which $R_3$ is a group Ib are obtained, for example, by reacting a compound of the formula R—$CH_2$—$X_1$ (IVea; $X_1$=reactive esterified hydroxy) with an alkali metal azide to form the corresponding compound of the formula R—$CH_2$—$N_3$ (IVeb) or with an alkali metal cyanide to form the corresponding compound of the formula R—$CH_2$$CH_2$—CH (IVec) and reducing the reaction product to the amine (IVe; $R_3$=R—$CH_2$— or R—$CH_2CH_2$—), for example by means of lithium aluminium hydride or, in the case of intermediates IVec, with hydrogen in the presence of Raney nickel or by means of borane/dimethyl sulphide.

Compounds IVe in which $R_3$ is a group Ia are manufactured, for example, by converting a corresponding carboxylic acid of the formula R—COOH (IVed) with thionyl chloride and then with an alkali metal azide into the corresponding compound of the formula R—$CON_3$ (IVee) and decomposing the latter, for example, by treatment with trifluoroacetic acid and then with an alkali metal hydroxide, to form the corresponding amine IVe ($R_3$=R).

Variant (d)

The C-acylation according to the process can be effected especially in the presence of one of the bases mentioned in Variant (a).

The reaction of compounds of the formula $R_3$—$X_1$ (IIa) with compounds of the formula

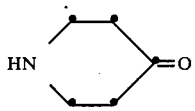
(Vc)

analogously to the N-substitution according to Variant (a) in the presence of one of the bases mentioned results in the starting material of the formula Va.

Variant (e)

Radicals $X_4$ that can be converted into $R_2$ are, for example, radicals that can be converted into a group $R_2$ by solvolysis, that is to say by reaction with a compound of the formula $R_2H$ (VIa) or a salt thereof, for example reactive esterified hydroxy groups, such as halogen atoms, for example chlorine, bromine or iodine. Radicals $X_4$ that can be converted into hydroxy are, furthermore, diazonium groups, for example of the formula —$N_2^\oplus A^\ominus$ in which $A^\ominus$ represents the anion of a strong acid, such as a mineral acid, for example the chloride or sulphate ion, or etherified or acylated hydroxy groups $R_2$ or optionally acylated amino groups $R_2$.

The solvolysis is effected in customary manner, for example in the presence of a base, such as an alkali metal or alkaline earth metal hydroxide, for example sodium or potassium hydroxide, or a tertiary nitrogen base, for example a tri-lower alkylamine, such as triethylamine, or a heteroaromatic nitrogen base, such as pyridine, or a quaternary ammonium hydroxide, such as benzyltrimethylammonium hydroxide, or by using the compound VIa in the form of a metal salt, for example of the formula $R_2^\ominus M^\oplus$(VIb) in which $M^\oplus$ represents an alkali metal cation, such as the sodium ion. The operation is advantageously carried out in the presence of a solvent or diluent, for example in an excess of the reactant VIa and/or in an inert solvent that is miscible with the latter, if necessary while cooling or heating, for example in a temperature range of approximately from 0° to 120° C., and/or under inert gas, such as nitrogen.

For the manufacture of starting compounds of the formula VI and the salts thereof, for example compounds of the formula $R_3$–$X_1$ (IIa) are used as starting materials and are reacted with a corresponding compound of the formula

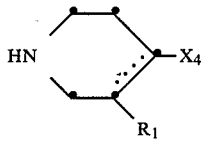

(VIa)

in the presence of one of the bases mentioned above.

Variant (f)

The anion $A^\ominus$ is, for example, the anion of a strong protonic acid, for example a halide ion, such as chloride, bromide or iodide, or a sulphonate ion, such as an optionally substituted lower alkane- or benzenesulphonate ion, for example the methanesulphonate, ethanesulphonate or p-bromobenzene-sulphonate or p-toluenesulphonate ion. $R_2''$ is especially etherified hydroxy $R_2$ or protected hydroxy. Protected hydroxy is, for example, silyloxy, such as tri-lower alkylsilyloxy, for example trimethylsilyloxy, but may also be triphenyl-lower alkoxy, for example trityloxy. Protected amino is, for example, silylamino, such as tri-lower alkylsilylamino, for example trimethylsilylamino, but may also be phenyl-, diphenyl- or triphenyl-lower alkylamino, such as benzylamino, diphenylamino or tritylamino.

The reduction of the excess double bonds is effected by treatment with a suitable reducing agent, for example by hydrogenation in the presence of a hydrogenation catalyst, by reduction with a hydride-transfer reagent or by reduction with a metallic reduction system consisting of metal and proton-removing agent.

Hydrogenation catalysts that come into consideration are, for example, elements of sub-group VIII of the Periodic Table of Elements or derivatives thereof, such as palladium, platinum, platinum oxide, ruthenium, rhodium, tris(triphenylphosphine)rhodium(I) halide, for example chloride, or Raney nickel, which are optionally supported on a carrier, such as activated carbon, alkali metal carbonate or sulphate or a silica gel. Suitable as hydride-transfer agents are, for example, suitable light metal hydrides, especially alkali metal aluminium hydrides or borohydrides, such as lithium aluminium hydride, lithium triethylborohydride, sodium borohydride, sodium cyanoborohydride, or tin hydrides, such as triethyl- or tributyl-tin hydride, or diborane. The metal component of the metallic reduction system is, for example, a base metal, such as an alkali metal or alkaline earth metal, for example lithium, sodium, potassium, magnesium or calcium, or a transition metal, for example zinc, tin, iron or titanium, whilst as proton-removing agents there are suitable, for example, protonic acids of the kind mentioned hereinbefore, such as hydrochloric or acetic acid, lower alkanols, such as ethanol, and/or amines or ammonia. Such systems are, for example, sodium/ammonia, zinc/hydrochloric acid, zinc/acetic acid or zinc/ethanol.

The manufacture of starting compounds of the formula VII is effected, for example, by reacting compounds of the formula $R_3$—$X_1$ (IIa; $X_1$ = A) with compounds of the formula

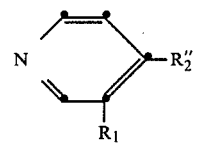

(VIIa)

or a salt thereof.

In the starting materials of the formulae IIb, III and IIIa, a hydroxy group $R_2$ may be in etherified form and a hydroxy or amino group $R_2$ may also be in intermediately protected form, as may also hydroxy or amino groups in starting materials of the formula VII or VIIa. Protected hydroxy is, for example, silyloxy, such as tri-lower alkylsilyloxy, for example trimethylsilyloxy, but may also be triphenyl-lower alkoxy, for example trityloxy. Protected amino is, for example, silylamino, such as tri-lower alkylsilylamino, for example trimethylsilylamino, but may also be phenyl-, diphenyl- or triphenyl-lower alkylamino, such as benzylamino, diphenylmethylamino or tritylamino.

The freeing of intermediately protected radicals, that is to say the removal of the intermediate protecting groups, is effected in customary manner, for example by solvolysis, such as mild hydrolysis, for example treatment with water under neutral or slightly acid conditions, for example by the action of dilute aqueous mineral or carboxylic acids, for example dilute hydrochloric or acetic acid.

Compounds according to the invention that are obtainable according to the process or by other means can be converted in customary manner into other compounds according to the invention.

For example, esterified or amidated carboxy groups $R_1$ can be hydrolysed to carboxy in customary manner, for example in the presence of a basic or acidic hydrolysing agent, such as an alkali metal hydroxide or carbonate, for example sodium hydroxide or potassium carbonate, or a mineral acid, for example hydrochloric acid or sulphuric acid. Esterified carboxy groups can also be converted into other esterified carboxy groups $R_1$ by transesterification, that is to say treatment with an alcohol in the presence of an acidic or basic solvolysing agent, such as a mineral acid, for example sulphuric acid, or a corresponding alkali metal alcoholate or an alkali metal hydroxide, or converted into amidated carboxy by reaction with ammonia or a corresponding amine.

Free carboxy $R_1$ can be converted into esterified carboxy in customary manner, for example by treatment with a corresponding alcohol in the presence of a mineral acid, for example sulphuric acid, or by conversion into a halide and subsequent reaction with a corresponding alcohol, for example in the presence of pyridine or triethylamine, or by conversion into an alkali metal salt and subsequent reaction with a reactive ester of the corresponding alcohol, such as a corresponding halide. Likewise, a carboxy compound can be esterified using a dehydrating agent, such as N,N-dicyclohexylcarbodiimide, with a corresponding alcohol. Free or esterified carboxy can also be converted into amidated carboxy by reaction with ammonia or an amine having at least one hydrogen atom and dehydration of the intermediately formed ammonium salt, for example by heating or by means of a dehydrating agent, such as N,N-dicyclohexylcarbodiimide, or by conversion into the halide and subsequent reaction with ammonia or an amine having at least one hydrogen atom.

Furthermore, hydroxy which may be present at the radical R or R' can be esterified, for example converted by treatment with a lower alkanecarboxylic acid anhydride or halide into lower alkanoyloxy or converted by reaction with a reactive ester, especially a hydrobromic or hydrochloric acid ester, of a lower alkanol into corresponding etherified hydroxy. In an analogous manner, a hydroxy or amino group $R_2$ may be acylated, for example converted by treatment with a lower alkanecarboxylic acid anhydride or halide or a lower alkanesulphonic acid chloride into lower alkanoyloxy or lower alkenesulphonyloxy, and hydroxy $R_2$ may be etherified. Conversely, in esterified or etherified hydroxy groups, such as lower alkanoyloxy or lower alkoxy, the hydroxy group may be freed by solvolysis, preferably under acidic conditions. In an analogous manner, it is also possible to hydrolyse etherified or acylated hydroxy $R_2$ to hydroxy, or acylated amino to amino. Furthermore, a hydroxy group that is etherified by a phenyl-lower alkanol or esterified by a carbonic acid semiester can be freed by hydrolysis.

If the dotted line indicates that there is a double bond in the compounds according to the invention, this bond can be hydrogenated to a single bond, for example in a manner known per se using a reducing agent, for example of the kind mentioned in Variant (f), especially with sodium borohydride or by catalytic hydrogenation.

Salts of compounds of the formula I and their tautomers can be manufactured in a manner known per se. For example, acid addition salts of compounds of the formula I are obtained by treatment with an acid or a suitable ion-exchange reagent. Salts can be converted in customary manner into the free compounds, acid addition salts, for example, by treatment with a suitable basic agent.

Depending on the procedure and the reaction conditions, the compounds according to the invention may be obtained with salt-forming, especially basic, properties, in free form or in the form of salts.

Owing to the close relationship between the novel compound in free form and in the form of its salts, hereinbefore and hereinafter there is to be understood by the free compound or its salts, where appropriate with regard to meaning and purpose, optionally also the corresponding salts or the free compound, respectively.

The novel compounds, including the salts of salt-forming compounds, may also be obtained in the form of their hydrates or include other solvents used for crystallisation.

Depending on the starting materials and procedures chosen, the novel compounds may be in the form of one of the possible isomers or in the form of mixtures thereof, for example depending on the number of asymmetric carbon atoms, in the form of pure optical isomers, such as antipodes, or in the form of isomeric mixtures, such as racemates, diastereoisomeric mixtures or mixtures of racemates.

Resulting diastereoisomeric mixtures and mixtures of racemates can be separated in known manner into the pure isomers, diastereoisomers or racemates on the basis of the physico-chemical differences between the components, for example by fractional crystallisation.

Resulting enantiomeric mixtures can be split into the optical antipodes according to known methods, for example by recrystallisation from an optically active solvent, chromatography on chiral adsorbents, with the aid of suitable microorganisms, by cleavage with specific, immobilised enzymes, by means of the formation of inclusion compounds, for example using chiral Crown ethers, with only one enantiomer being complexed, or by conversion into diastereoisomeric salts, for example by reacting a basic end product racemate with an optically active acid, such as carboxylic acid, for example tartaric or malic acid, or sulphonic acid, for example camphorsulphonic acid, and separating the diastereoisomeric mixture obtained in that manner into the diastereoismers, for example on the basis of their differing solubility, from which diastereoisomers the desired enantiomer can be freed by the action of suitable agents. Advantageously, the more active enantiomer is isolated.

The invention relates also to those embodiments of the process according to which a compound obtainable as an intermediate at any stage of the process is used as starting material and the remaining steps are carried out or a starting material is used in the form of a derivative or salt and/or in the form of its racemates or antipodes, or, especially, is formed under the reaction conditions.

The starting materials used in the process of the present invention are preferably those which result in the compounds described at the beginning as being especially valuable. The invention relates also to novel starting materials which have been developed specifically for the manufacture of the compounds according to the invention, their use and processes for their manufacture, the variables R, R', $R_1$, $R_2$, $R_3$, $alk_1$ and $alk_2$ and also the substituents of R and R' having the meanings given for the compound groups of the formula I that are preferred in each case.

In this connection there may be mentioned especially compounds of the formula

(IVc)

and their salts. These also exhibit nootropic properties comparable in their strength of action to that of the corresponding compounds of the formula I or I' and may also be used as nootropically active ingredients in medicaments.

The invention accordingly relates also to compounds of the formula IVc in which $R_1$ represents carboxy, lower alkoxycarbonyl, carbamoyl, N-lower alkylcarbamoyl or N,N-di-lower alkylcarbamoyl, $R_3$ represents a radical of the formula R- (Ia), R-$alk_1$- (Ib) or R'=$alk_2$-

(Ic) in which R represents a benzocycloalkenyl radical having a total of from 8 to 12 ring carbon atoms which is bonded via a saturated carbon atom and which is unsubstituted or is mono- or poly-substituted in the benzo moiety by hydroxy, lower alkoxy, lower alkanoyloxy, halogen, lower alkyl and/or by trifluoromethyl, and/or substituted in the α-position by lower alkyl, and R' represents a benzocycloalkylidene radical having a total of from 8 to 12 ring carbon atoms which is unsubstituted or is mono- or poly-substituted in the benzo moiety by hydroxy, lower alkoxy, lower alkanoyloxy, halogen, lower alkyl and/or by trifluoromethyl, and $alk_1$ represents lower alkylene or lower alkylidene and $alk_2$ represents a lower alkyl-ω-ylidene radical, with the proviso that, in compounds of the formula IVc in which $R_3$ represents a group Ia, R is other than indan-2-yl which is unsubstituted or is monosubstituted in the 5-position by halogen, lower alkyl or by lower alkoxy when $R_1$ represents lower alkoxycarbonyl or carbamoyl, and their salts, to the use of these compounds, to processes for their manufacture and to pharmaceutical compositions containing a compound of the formula IVc or a pharmaceutically acceptable salt thereof.

The variables of the formula IVc have, for example, the preferred meanings given under formula I.

The invention relates in this respect especially to compounds of the formula IVc in which R and R' each represents a benzocyclobuten-1-yl radical, benzocyclobuten-1-ylidene radical, indan-1-yl or indan-2-yl radical or a 1,2,3,4-tetrahydronaphth-1-yl or 1,2,3,4-tetrahydronaphth-2-yl radical each of which is unsubstituted or is mono- or poly-substituted, for example di- or tri-substituted, in the benzo moiety by hydroxy, lower alkoxy, lower alkanoyloxy and/or by halogen, and/or substituted in the α-position by lower alkyl, $R_1$ represents carboxy, lower alkoxycarbonyl or carbamoyl, and $alk_1$ represents lower alkylene or lower alkylidene which in each case connects the two ring systems by 1 or 2, respectively, up to and including 3 carbon atoms, and $alk_2$ represents lower alkyl-ω-ylidene which connects the two ring systems by 2 or 3 carbon atoms, and their salts.

The invention relates in this respect above all to compounds of the formula IVc in which $R_3$ represents a group Ia or Ib, R represents a benzocyclobuten-1-yl radical, an indan-1-yl radical or, secondly, an indan-2-yl radical or a 1,2,3,4-tetrahydronaphth-1-yl radical which is unsubstituted or is monosubstituted in the benzo moiety by lower alkoxy having up to and including 4 carbon atoms, such as methoxy, lower alkyl having up to and including 4 carbon atoms, such as methyl, or by halogen having an atomic number of up to and including 35, such as chlorine, or disubstituted in the benzo moiety by lower alkyl having up to and including 4 carbon atoms, such as methyl, or by lower alkoxy having up to and including 4 carbon atoms, such as methoxy, and also by lower alkyl having up to and including 4 carbon atoms, such as methyl, $R_1$ represents lower alkoxycarbonyl, especially having from 2 up to and including 5 carbon atoms, such as ethoxycarbonyl, or carbamoyl, and $alk_1$ represents lower alkylene which bridges the ring systems by from 1 up to and including 3 carbon atoms, especially having up to and including 3 carbon atoms, such as methylene, and their salts.

The invention relates in this respect first and foremost to compounds of the formula IVc in which $R_3$ represents a group of the formula Ib, R represents a benzocyclobuten-1-yl radical which is unsubstituted or is monosubstituted in the benzo moiety, especially in the 5-position, by lower alkoxy having up to and including 4 carbon atoms, such as methoxy, $R_1$ represents lower alkoxycarbonyl having from 2 up to and including 5 carbon atoms, such as ethoxycarbonyl, and $alk_1$ represents methylene or ethylene, and their salts.

The invention relates preferably to the novel compounds of the formula IVc mentioned in the Examples and to processes for their manufacture.

The present invention relates also to processes for the manufacture of compounds of the formula IVc, their tautomers and their salts, for example characterised in that (g) compounds of the formulae $R_3—Z_1$ (VIIIa) and $Z_2—CH_2—CH(Z_3)—R_1$ (VIIIb), in which one of the radicals $Z_1$ and $Z_2$ represents reactive esterified hydroxy, the other represents amino and $Z_3$ represents hydrogen, or $Z_1$ is amino and $Z_2$ and $Z_3$ together represent an additional bond, are reacted with each other and, if desired, a compound obtainable according to the process or in a different manner is converted into a different compound of the formula IVc, an isomeric mixture obtainable according to the process is separated into its components, an enantiomeric or diastereoisomeric mixture obtainable according to the process is split into the enantiomers or diastereoisomers, respectively, a free compound obtainable according to the process is converted into a salt and/or a salt obtainable according to the process is converted into the free compound or into a different salt.

Reactive esterified hydroxy is especially hydroxy esterified by a strong inorganic acid or organic sulphonic acid, for example halogen, such as chlorine, bromine or iodine, sulphonyloxy, such as hydroxysulphonyloxy, halosulphonyloxy, for example fluorosulphonyloxy, lower alkanesulphonyloxy optionally substituted, for example, by halogen, for example methane- or trifluoromethane-sulphonyloxy, cycloalkanesulphonyloxy, for example cyclohexanesulphonyloxy, or benzenesulphonyloxy optionally substituted, for example, by lower alkyl or by halogen, for example p-bromophenyl- or p-toluene-sulphonyloxy.

The reaction is carried out in this case especially in the presence of a condensation agent, such as a suitable base. Suitable bases are, for example, alkali metal hydroxides, hydrides, amides, alkoxides, carbonates, triphenylmethylides, di-lower alkylamides, amino-lower alkylamides or lower alkylsilylamides, naphthaleneamines, lower alkylamines, basic heterocycles, ammonium hydroxide and also carbocyclic amines. There may be mentioned by way of example sodium hydroxide, hydride, amide or ethoxide, potassium tert.butoxide or carbonate, lithium triphenylmethylide, lithium diisopropylamide, potassium 3-(aminopropyl)amide or bis-(trimethylsilyl)-amide, dimethylaminonaphthalene, di- or tri-ethylamine, pyridine, benzyltrimethylammonium hydroxide, 1,5-diaza-bicyclo[4.3.0]non-5-ene (DBN) and also 1,8-diaza-bicyclo[5.4.0]undec-7-ene (DBU). The reaction of amines VIIIa ($Z_1$=amino) with acrylic acid compounds XXI ($Z_2+Z_3$=bond) is effected, for example, while heating, for example at approximately 60°–120° C.

Starting materials VIIIa are identical with compounds IIa and IVe the manufacture of which is indicated in Variants (a) and (c), respectively.

As subsequent operations that may, if desired, be carried out on compounds IVc obtainable according to the process there may be mentioned, especially, conversion reactions of R or R' and $R_1$, separation of enantiomers and diastereoisomers and inter-conversions of salts and free compounds analogous in each case to those given for the compounds of the formula I, which may also be carried out in an analogous manner.

The invention relates also to the use of compounds of the formula I and IVc, or their tautomers or pharmaceutically acceptable salts of such compounds having salt-forming properties, as pharmacologically, especially nootropically, active substances. They can be used, preferably in the form of pharmaceutically acceptable preparations, in a method for the prophylactic and/or therapeutic treatment of the animal or human body, especially as nootropics, for example for the treatment of memory disorders.

The invention relates also to pharmaceutical preparations that contain the compounds according to the invention or pharmaceutically acceptable salts thereof as active ingredients, and to processes for their manufacture.

The pharmaceutical preparations according to the invention which contain the compounds according to the invention or pharmaceutically acceptable salts thereof are those for enteral, such as oral and also rectal, administration and for parenteral administration to (a) warm-blooded animal(s), the pharmacological active ingredient being present on its own or together with a pharmaceutically acceptable carrier. The daily dosage of the active ingredient depends on the age and the individual condition and also on the mode of administration.

The novel pharmaceutical preparations contain, for example, from approximately 10% to approximately 80%, preferably from approximately 20% to approximately 60%, active ingredient. Pharmaceutical preparations according to the invention for enteral or parenteral administration are, for example, those in dosage unit form, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, if desired granulating a resulting mixture, and processing the mixture or granulate, if desired or necessary, after the addition of suitable adjuncts, to form tablets or dragée cores.

Suitable carriers are especially fillers, such as sugars, for example lactose, saccharose, mannitol or sorbitol, cellulose preparations and/or calcium phosphate, for example tricalcium phosphate or calcium hydrogen phosphate, and also binders, such as starch pastes using, for example, corn, wheat, rice or potato starch, gelatine, tragacanth, methylcellulose and/or polyvinylpyrrolidone, if desired disintegrating agents, such as the above-mentioned starches, and also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that may be resistant to gastric juices, there being used, inter alia, concentrated sugar solutions optionally containing gum arabic, talc, polyvinylpyrrolidone, polyethylene glycol and/or titanium dioxide, lacquer solutions in suitable organic solvents or solvent mixtures or, for the manufacture of coatings that are resistant to gastric juices, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical preparations are dry-fill capsules consisting of gelatine, and also soft sealed capsules consisting of gelatine and a plasticiser, such as glycerin or sorbitol. The dry-fill capsules may contain the active ingredient in the form of a granulate, for example in admixture with fillers, such as lactose, binders, such as starches, and/or glidants, such as talc or magnesium stearate, and, optionally, stabilisers. In soft capsules, the active ingredient is preferably dissolved or suspended in suitable liquids, such as fatty oils, paraffin oil or liquid polyethylene glycols, it also being possible to add stabilisers.

Rectally administrable pharmaceutical preparations that come into consideration are, for example, suppositories which consist of a combination of the active ingredient and a suppository base material. Suitable suppository base materials are, for example, natural or synthetic triglycerides, paraffin hydrocarbons, polyethylene glycols or higher alkanols. It is also possible to use gelatine rectal capsules which contain a combination of the active ingredient with a base material. Suitable base materials are, for example, liquid triglycerides, polyethylene glycols or paraffin hydrocarbons.

Especially suitable for parenteral administration are aqueous solutions of an active ingredient in water-soluble form, for example in the form of a water-soluble salt, and also suspensions of the active ingredient, such as corresponding oily injection suspensions, with suitable lipophilic solvents or vehicles, such as fatty oils, for example sesame oil, or synthetic fatty acid esters, such as ethyl oleate or triglycerides, being used, or aqueous injection suspensions containing substances that increase the viscosity, for example sodium carboxymethylcellulose, sorbitol and/or dextran, and, optionally, also stabilisers.

The dosage of the active ingredient depends on the species of warm-blooded animal, the age and individual condition and also on the mode of administration. In normal circumstances, for a warm-blooded animal weighing approximately 75 kg, in the case of oral administration, an approximate daily dosage of from about 20 to about 500 mg, especially from about 25 to about 250 mg, advantageously in several equal partial doses, is to be recommended.

The following Examples illustrate the invention described above; they are not intended, however, to limit the scope thereof in any way. Temperatures are given in degrees Celsius.

EXAMPLE 1

18 g (49 mmol) of N-[(5-methoxybenzocyclobuten-1-yl)methyl]-imino-di-(3-propionic acid) diethyl ester dissolved in 100 ml of toluene are added dropwise to a suspension of 3 g (63 mmol) of sodium hydride (50% dispersion in mineral oil) in 300 ml of toluene. The reaction mixture is heated, while stirring, to an internal temperature of approximately 110°, the ethanol produced being distilled off. Thereupon, the reaction mixture is allowed to cool, is diluted with ethyl acetate and, while stirring, 100 ml of water are added. The organic phase is separated off, dried over magnesium sulphate and concentrated by evaporation. The crude material so obtained is purified by chromatography and converted with ethanolic hydrochloric acid into the hydrochloride. Crystallisation from ethanol yields 4-hydroxy-1-[(5-methoxybenzocyclobuten-1-yl)methyl]1,2,5,6-tetrahydro-pyridine-3-carboxylic acid ethyl ester hydrochloride aliasl-[(5-methoxybenzocyclobuten-1-yl)methyl]-4-oxo-piperidine-3-carboxylic acid ethyl ester hydrochloride of m.p. 181°–182°.

The starting material can be manufactured, for example, in the following manner:

245 ml (2.26 mol) of ethyl acrylate are added dropwise, while stirring, to 123 g (752 mmol) of 5-methoxybenzocyclobuten-1-ylmethylamine in 1100 ml of ethanol. Heating is then carried out under reflux for 20 hours. The reaction mixture is concentrated under a water-jet vacuum and is then purified by chromatography. The material so purified is converted with ethanolic hydrochloric acid into the hydrochloride and crystallised from ethanol/diethyl ether. N-[(5-methoxybenzocyclobuten-1-yl)methyl]imino-di-(3-propionic acid) diethyl ester hydrochloride of m.p. 97°–98.5° C. is obtained.

EXAMPLE 2

4-hydroxy-1-[(5-methoxybenzocyclobuten-1-yl)methyl]-1,2,5,6-tetrahydro-pyridine-3-carboxylic acid methyl ester hydrochloride alias 1-[(5-methoxybenzocyclobuten-1-yl)methyl]-4-oxo-piperidine-3-carboxylic acid methyl ester hydrochloride of m.p. 114.2°–116.4° can be manufactured analogously to Example 1 from 3.6 g (74 mmol) of sodium hydride (50% dispersion in mineral oil) and 19.2 g (57 mmol) of N-[(5-methoxybenzocyclobuten-1-yl)methyl]imino-di-(3-propionic acid) dimethyl ester in 300 ml of toluene.

The starting material, N-[(5-methoxybenzocyclobuten-1-yl)methyl]imino-di-(3-propionic acid) dimethyl ester hydrochloride of m.p. 114°–115 5° C. can be manufactured in a manner analogous to that described in Example 1 from 4.2 g (25 mmol) of 5-methoxybenzocyclobuten-1-ylmethylamine and 6.8 ml (76 mmol) of methyl acrylate in 50 ml of methanol.

EXAMPLE 3

11.7 g (33 mmol) of 4-hydroxy-1-[(5-methoxybenzocyclobuten-1-yl)methyl]-1,2,5,6-tetrahydro-pyridine-3carboxylic acid ethyl ester hydrochloride are hydrogenated at 4·10$^5$ Pa and room temperature with the addition of 1.2 g of platinum oxide in 300 ml of ethanol. The catalyst is filtered off and the reaction solution is concentrated. Crystallisation from ethanol/diethyl ether yields cis-4-hydroxy-1-[(5-methoxybenzocyclobuten-1-yl)methyl]-piperidine-3-carboxylic acid ethyl ester hydrochloride of m.p. 156°–160°.

EXAMPLE 4

10.6 g (33.4 mmol) of 4-hydroxy-1-[(5-methoxybenzocyclobuten-1-yl)methyl]-1,2,5,6-tetrahydro-pyridine-3carboxylic acid ethyl ester dissolved in 40 ml of ethanol are added dropwise to a solution of 0.7 g (17 mmol) of sodium borohydride in 160 ml of ethanol/water (1:1). The reaction mixture is stirred at room temperature for 3 hours, then diluted with 200 ml of water and extracted with dichloromethane. The combined extracts are dried over sodium sulphate and concentrated by evaporation under reduced pressure. Purification by chromatography on silica gel yields, in addition to the cis-derivative described in Example 3, also the trans-4-hydroxy-1-[(5-methoxybenzocyclobuten-1-yl)methyl]-piperidine-3-carboxylic acid ethyl ester in the form of a viscous oil, Rf=0.44, hexane/ethanol (4:1).

EXAMPLE 5

1.1 ml (14 mmol) of methanesulphonic acid chloride are added dropwise, while stirring at room temperature, to 4 g (12.5 mmol) of cis-4-hydroxy-1-[(5-methoxybenzocyclobuten-1-yl)methyl]-piperidine-3-carboxylic acid ethyl ester hydrochloride, 1.7 g (14 mmol) of 4-dimethylaminopyridine and 3.5 ml (25 mmol) of triethylamine in 100 ml of dichloromethane. Stirring is continued at that temperature until the reaction is complete.

The reaction mixture is concentrated, 4 g of potassium hydroxide in 50 ml of ethanol are added and the whole is stirred for 30 minutes. The mixture is then diluted with dichloromethane and washed with water. The organic phase is separated off, dried over magnesium sulphate and concentrated under reduced pressure. The resulting crude product is purified by chromatography on silica gel, converted into the hydrochloride with ethanolic hydrochloric acid and crystallised from ethanol/diethyl ether. 1-[(5-methoxybenzocyclobuten-1-yl)methyl]-1,2,5,6-tetrahydro-pyridine-3-carboxylic acid ethyl ester hydrochloride of m.p. 204.5°–205.5° is obtained.

EXAMPLE 6

4-hydroxy-1-[2-(5-methoxybenzocyclobuten-1-yl)ethyl]-1,2,5,6-tetrahydro-pyridine-3-carboxylic acid ethyl ester hydrochloride and 1-[2-(5-methoxybenzocyclobuten-1-yl)ethyl]-4-oxo-piperidine-3-carboxylic acid ethyl ester hydrochloride of m.p. 148°–150° can be manufactured analogously to Example 1 from 26.5 g (70 mmol) of N-[2-(5-methoxybenzocyclobuten-1-yl)ethyl]imino-di-(3-propionic acid) diethyl ester and 4.4 g (91 mmol) of sodium hydride (50% dispersion in mineral oil) in 250 ml of toluene.

The starting material can be manufactured, for example, as follows:

4.3 ml (43 mmol) of borane dimethyl sulphide (10M in tetrahydrofuran) are slowly added dropwise, at room temperature, to 5 g (29 mmol) of 2-(5-methoxybenzocyclobuten-1-yl)acetonitrile in 50 ml of tetrahydrofuran. The mixture is then heated under reflux for 30 minutes. Subsequently, while cooling well, 30 ml of 6N hydrochloric acid are added and the mixture is then heated under reflux for a further 30 minutes. The reaction mixture is cooled, adjusted to pH 10 with 4N sodium hydroxide solution and extracted with dichloromethane. The organic phases are combined, dried over sodium sulphate and concentrated under reduced pressure. 2-(5-methoxybenzocyclobuten-1-yl)ethylamine is obtained in the form of a viscous oil; Rf=0.1, toluene/ethanol/conc. aqueous ammonia (90:20:1).

N-[2-(5-methoxybenzocyclobuten-1-yl)ethyl]-iminodi-(3-propionic acid) diethyl ester is obtained in the form of a viscous oil from 12 g (68 mmol) of 2-(5-methoxybenzocyclobuten-1-yl)ethylamine and 22 ml (200 mmol) of ethyl acrylate; Rf=0.24, hexane/ethyl acetate (8:2).

EXAMPLE 7

Cis-4-hydroxy-1-[2-(5-methoxybenzocyclobuten-1-yl)ethyl]-piperidine-3-carboxylic acid ethyl ester hydrochloride of m.p. 144° can be manufactured analogously to Example 3 by hydrogenating 3.7 g (10 mmol) of 4-hydroxy-1-[2-(5-methoxybenzocyclobuten1-yl)ethyl]-1,2,5,6-tetrahydro-pyridine-3-carboxylic acid ethyl ester hydrochloride at 4·10⁵ Pa hydrogen overpressure and room temperature with the addition of 400 mg of platinum oxide in 100 ml of ethanol.

EXAMPLE 8

Trans-4-hydroxy-1-[2-(5-methoxybenzocyclobuten-1-yl)ethyl]-piperidine-3-carboxlic acid ethyl ester can be manufactured in the form of a viscous oil analogously to Example 4 from 3.3 g (10 mmol) of 4-hydroxy-1-[2-(5-methoxybenzocyclobuten-1-yl)ethyl]-1,2,5,6-tetrahydro-pyridine-3-carboxylic acid ethyl ester and 0:2 g (5 mmol) of sodium borohydride in 80 ml of 50% aqueous ethanol;
Rf=0.4, hexane/ethanol (8:2).

EXAMPLE 9

1-[2-(5-methoxybenzocyclobuten-1-yl)ethyl]-1,2,5,6-tetrahydro-pyridine-3-carboxylic acid ethyl ester hydrochloride of m.p. 150.5°–152.3° can be obtained analogously to Example 5 from 8 g (24 mmol) of cis-4-hydroxy-1-[2-(5-methoxybenzocyclobuten-1-yl)ethyl]-piperidine-3-carboxylic acid ethyl ester, 3.2 g (26 mmol) of 4-dimethylaminopyridine, 6.65 ml (48 mmol) of triethylamine and 2 ml (27 mmol) of methanesulphonic acid chloride in 200 ml of dichloromethane.

EXAMPLE 10

4-hydroxy-1-[2-(5-methoxybenzocyclobuten-1-yl)ethyl]-1,2,5,6-tetrahydropyridine-3-carboxylic acid methyl ester hydrochloride alias [2-(5-methoxybenzocyclobuten-1-yl)ethyl]-4-oxo-piperidine-3-carboxylic acid methyl ester hydrochloride of m.p. 157°–158.5° can be manufactured in a manner analogous to that described in Example 1 from 18.6 g (53 mmol) of N-[2-(5-methoxybenzocyclobuten-1-yl)ethyl]imino-di-(3-propionic acid) dimethyl ester and 3.3 g (69 mmol) of sodium hydride (50% dispersion in mineral oil) in 350 ml of toluene.

The starting material, N-[2-(5-methoxybenzocyclobuten-1-yl)ethyl]imino-di-(3-propionic acid) dimethyl ester of Rf=0.64, hexane/ethyl acetate (7:3), is obtained, for example, in a manner analogous to that described in Example 1, from 14 g (77 mmol) of 2-(5-methoxybenzocyclobuten-1-yl)ethylamine and 21 ml (230 mmol) of methyl acrylate in 150 ml of methanol.

EXAMPLE 11

3.5 g (10 mmol) of 4-hydroxy-1-[(5-methoxybenzocyclobuten-1-yl)methyl]-1,2,5,6-tetrahydro-pyridine-3-carboxylic acid ethyl ester hydrochloride in 50 ml of dioxan and 50 ml of 25% aqueous ammonia are heated in a bomb tube at 80° C., while stirring, for 48 hours. The reaction mixture is then extracted with trichloromethane; the extracts are washed with water, dried over sodium sulphate and concentrated under reduced pressure. The crude material is purified by chromatography, converted into the hydrochloride with hydrochloric acid and crystallised from methanol/diethyl ether. 4-amino-1-[(5-methoxybenzocyclobuten-1-yl)methyl]-1,2,5,6-tetrahydro-pyridine-3-carboxylic acid ethyl ester hydrochloride alias 1-(5-methoxybenzocyclobuten-1-yl)methyl]-4-imino-piperidine-3-carboxylic acid ethyl ester hydrochloride of m.p. 184°–184.5° is obtained

EXAMPLE 12

2.42 g (10 mmol) of methanesulphonic acid (5-methoxybenzocyclobuten-1-ylmethyl) ester, 1.7 g (10 mmol) of 4-piperidone-3-carboxylic acid ethyl ester and 1.38 g (10 mmol) of potassium carbonate are heated under reflux in 50 ml of ethanol for 24 hours. The mixture is then filtered, concentrated under a water-jet vacuum and chromatographed on silica gel. The material so obtained is converted into the hydrochloride with ethanolic hydrochloric acid and crystallised from ethanol. 4-hydroxy-1-[(5-methoxybenzocyclobuten-1-yl)methyl]-1,2,5,6-tetrahydro-pyridine-3-carboxylic acid ethyl ester hydrochloride alias 1-[2-(5-methoxybenzocyclo- buten-1-yl)methyl]-4-oxo-piperidine-3-carboxylic acid ethyl ester hydrochloride of m.p. 181°–182° is obtained.

The starting material can be obtained, for example, in the following manner:

6.1 ml (76 mmol) of pyridine and 3.6 ml (46 mmol) of methanesulphonic acid chloride are added at 0° C., while stirring, with the exclusion of moisture, to 5.0 g (30.5 mmol) of (5-methoxybenzocyclobuten-1-yl)methanol in 50 ml of dichloromethane. The mixture is then stirred at room temperature for a further 18 hours to complete the reaction. 50 ml of ice-water are then added and the whole is stirred for 30 minutes. The organic phase is separated off, washed once in each case with 2N sodium hydroxide solution, 2N hydrochloric acid and water, dried over sodium sulphate and concentrated under reduced pressure. Methanesulphonic acid (5-methoxybenzocyclobuten-1-ylmethyl) ester is obtained in the form of a viscous oil, Rf=0.4, toluene/ethyl acetate (9:1).

EXAMPLE 13

3-(5-methoxybenzocyclobuten-1-ylmethylamino)propionic acid ethyl ester hydrochloride of m.p. 129°–130° can be manufactured analogously to Example 1 from 3.6 g (22 mmol) of 5-methoxybenzocyclobuten-1-ylmethylamine and 2.4 ml (22 mmol) of ethyl acrylate in 70 ml of toluene at room temperature.

EXAMPLE 14

4.5 g (20 mmol) of 1-bromo-2-(indan-1-yl)-ethane are dissolved in 20 ml of toluene and added, at room temperature, to a solution of 4.9 g of guvacoline hydrobromide (20 mmol) and 5.7 g (44 mmol) of N,N-diisopropyl-N-ethylamine in 15 ml of dimethylformamide. The mixture is stirred at 45° under nitrogen for 12 hours. The solvents are then substantially removed under reduced pressure. The residue is rendered acidic with 2N hydrochloric acid and the aqueous solution is extracted with diethyl ether. The acidic aqueous phases are rendered basic with saturated sodium bicarbonate solution and extracted by shaking with diethyl ether. The organic phases are separated off, washed with saturated sodium chloride solution and dried over magnesium sulphate. 1-[2-(indan-1-yl)ethyl]-1,2,5,6-tetrahydropyridine-3-carboxylic acid methyl ester is obtained.

Ethereal hydrochloric acid is added to the resulting crude base, and the resulting hydrochloride is recrystallised from isopropanol/diethyl ether. 1-[2(indan-1-yl)ethyl]-1,2,5,6-tetrahydro-pyridine-3carboxylic acid methyl ester hydrochloride of m.p. 195°–197° is obtained.

EXAMPLE 15

5.13 g (20 mmol) of methanesulphonic acid (6-methoxyindan-1-ylmethyl) ester are dissolved in 20 ml of toluene and added to a solution of 4.9 g (22 mmol) of guvacoline hydrobromide in 15 ml of dimethylformamide and 5.65 g (44 mmol) of N,N-diisopropyl-N-ethylamine. The reaction mixture is stirred at 50° under nitrogen for 24 hours. The solvents are then substantially removed under reduced pressure. The residue is dissolved in 2N hydrochloric acid, the acidic solution is extracted by shaking with diethyl ether and the ethereal phases are separated off. The acidic aqueous solution is rendered basic with saturated sodium bicarbonate solution and extracted with diethyl ether. The ethereal solutions are subsequently washed with saturated sodium chloride solution, dried over magnesium sulphate and concentrated to dryness by evaporation in vacuo. The resulting residue is purified on silica gel with dichloromethane/methanol (19:1) and the resulting eluates are concentrated to dryness by evaporation. The resulting 1-[(6-methoxyindan-1-yl)methyl]-1,2,5,6-tetrahydro-pyridine-3-carboxylic acid methyl ester is dissolved in diethyl ether and oxalic acid is added thereto. The oxalate which precipitates is recrystallised from isopropanol/water and from diethyl ether. 1-[(6-methoxyindan-1-yl)methyl]-1,2,5,6-tetrahydro-pyridine-3-carboxylic acid methyl ester oxalate of m.p. 184°-186° is obtained The necessary starting materials are obtained, for example, as follows:

30.9 g (0.15 mol) of 6-methoxyindane-1-carboxylic acid methyl ester are dissolved in 600 ml of diethyl ether and added dropwise in the course of 1 hour to a suspension of 8.5 g (0.22 mol) of lithium aluminium hydride in 300 ml of diethyl ether, during which the mixture comes to reflux. The mixture is maintained under reflux for 15 hours, is cooled with an ice bath and treated in succession with 8.5 ml of water, 8.5 ml of 15% sodium hydroxide solution and 25 ml of water.

The resulting white, flocculent suspension is filtered off, and the residue is boiled up twice with diethyl ether and again filtered off. The organic phases are dried over magnesium sulphate and concentrated by evaporation in vacuo. The resulting residue, a colourless viscous oil, is crude 6-methoxyindane-1-methanol.

5.7 g (32 mmol) of crude 6-methoxyindane-1-methanol are dissolved in 50 ml of dichloromethane, and a solution of 4.3 g (38 mmol) of methanesulphonic acid chloride in 10 ml of dichloromethane is added thereto. The mixture is cooled to +5° with an ice bath and, in the course of 20 minutes, a solution of 3.9 g (38 mmol) of triethylamine in 10 ml of dichloromethane is added dropwise. The mixture is stirred at room temperature for 3 hours, the triethylammonium chloride which has precipitated is filtered off and the filtrate is extracted by shaking with ice-water. The organic phase is dried over magnesium sulphate and concentrated to dryness by evaporation under reduced pressure. The resulting oil consists of crude methanesulphonic acid (6-methoxyindan-1-ylmethyl) ester, which is further reacted immediately.

EXAMPLE 16

5.23 g (15 mmol) of N-[(6-methoxyindan-1-yl)methyl]imino-di-(3-propionic acid) dimethyl ester are dissolved in 150 ml of toluene and 0.72 g (15 mmol) of sodium hydride (50% dispersion in mineral oil) is added thereto. The reaction mixture is heated at 80° for 3 hours and then, at an internal temperature of 110°, a mixture of methanol and toluene is distilled off.

The resulting residue is poured onto ice/hydrochloric acid and the organic phase is separated off. The acidic aqueous solution is rendered basic with sodium bicarbonate solution and extracted by shaking with diethyl ether/ethyl acetate. The organic phases are washed with saturated sodium chloride solution, dried over magnesium sulphate and concentrated to dryness by evaporation under reduced pressure. The resulting residue consists of crude 4-hydroxy-1-[(6-methoxyindan-1-yl)methyl]-1,2,5,6-tetrahydro-pyridine- and 1-[(6-methoxyindan-1-yl)methyl]-4-oxo-pyridine-3-carboxylic acid methyl ester. The resulting crude base is purified on 6 g of silica gel with cyclohexane as eluant and converted into the hydrochloride with ethereal hydrochloric acid. The hydrochloride is recrystallised from isopropanol/diethyl ether. The pure 4-hydroxy-1-[(6-methoxyindan-1-yl)methyl]-1,2,5,6-tetrahydro-pyridine-alias 1-[(6-methoxyindan-1-yl)-methyl]-4-oxo-piperidine-3-carboxylic acid methyl ester hydrochloride melts at 175°-178°.

The starting material can be obtained, for example, as follows:

12.8 g (50 mmol) of methanesulphonic acid (6-methoxyindan-1-ylmethyl) ester and 5.2 g (80 mmol) of sodium azide are dissolved in 130 ml of dimethyl sulphoxide and stirred at 80° for 1 hour. The reaction mixture is poured onto ice-water and extracted by shaking with diethyl ether. The organic phases are washed twice with saturated sodium chloride solution, dried over magnesium sulphate and concentrated to dryness by evaporation under reduced pressure. 9.7 g of crude, oily 6-methoxyindan-1-ylmethylazide are obtained as residue.

20 g (0.1 mol) of 6-methoxyindan-1-ylmethylazide are dissolved in 400 ml of diethyl ether and added dropwise, at 25°-30°, to a suspension of 5.0 g (0.13 mol) of lithium aluminium hydride in 200 ml of diethyl ether. When the addition has been completed, the mixture is maintained under reflux for 6 hours and, while cooling with ice, 5 ml of water, 5 ml of 15% sodium hydroxide solution and 15 ml of water are added thereto. The white precipitate which has formed is filtered off and boiled up 3 times with dichloromethane. The organic filtrates are combined, dried over magnesium sulphate and concentrated to dryness by evaporation in vacuo. The N-(6-methoxyindan-1-ylmethyl)amine which is obtained as an oily residue is converted into the hydrochloride with ethereal hydrochloric acid and recrystallised from isopropanol/diethyl ether. The pure 6-methoxyindan-1ylmethylammonium chloride melts at 129°-131°.

5.1 g (28.7 mmol) of 6-methoxyindan-1-ylmethylamine which has been manufactured from the latter are dissolved together with 7.4 g (86 mmol) of methyl acrylate in 60 ml of methanol and the whole is heated under reflux for 12 hours. The reaction mixture is concentrated by evaporation and the residue is purified with cyclohexane over 10 g of silica gel. The resulting crude N-[(6-methoxyindan-1-yl)methyl]imino-di-(3-propionic acid) dimethyl ester is further used in crude form.

EXAMPLE 17

4-hydroxy-1-[(6-methoxyindan-1-yl)methyl]-1,2,5,6-tetrahydro-pyridine-alias 1-[(6-methoxyindan-1-yl)methyl]-4-oxo-piperidine-3-carboxylic acid ethyl ester is obtained analogously to Example 16 from 9.9 g (26 mmol) of N-[(6-methoxyindan-1-yl)methyl]imino-di-(3-propionic acid) diethyl ester and 1.63 g (34 mmol) of sodium hydride suspension.

The hydrochloride is precipitated from the crude base using ethereal hydrochloric acid and is recrystallised from isopropanol/diethyl ether. The pure 4-hydroxy-1-[(6-methoxyindan-1-yl)methyl]-1,2,5,6-tetrahydro-pyridine- and 1-[(6-methoxyindan-1-yl)methyl]-4-oxo-piperidine-3-carboxylic acid ethyl ester hydrochloride melts at 155°–156°.

The starting material is obtained, for example, as follows:

10.2 g (56 mmol) of 6-methoxyindan-1-ylmethylamine and 17.2 g (172 mmol) of ethyl acrylate are dissolved in 120 ml of ethanol and maintained under reflux for 24 hours. The reaction product is concentrated to dryness by evaporation in vacuo and the resulting oily N-[(6-methoxyindan-1-yl)methyl]imino-di-(3-propionic acid) diethyl ester is purified on 20 g of silica gel with cyclohexane.

EXAMPLE 18

11.6 g (30 mmol) of N-[2-(6-methoxyindan-1-yl)ethyl]imino-di-(3-propionic acid) diethyl ester are dissolved in 100 ml of toluene and added dropwise, at room temperature, to a suspension of 1.85 g (39 mmol) of a 50% sodium hydride dispersion in 50 ml of toluene. The reaction mixture is heated at 80° for 3 hours the external temperature is then increased to 110°–120° and a mixture of ethanol and toluene is distilled off. The residue is cooled and poured onto 100 ml of ice-cold N hydrochloric acid. The aqueous phase is separated off, the organic phase is extracted twice by shaking with 30 ml of N hydrochloric acid each time and the acidic aqueous portions are combined and rendered alkaline with saturated sodium bicarbonate solution. After extracting by shaking with diethyl ether/ethyl acetate, the organic phases are washed with saturated sodium chloride solution and dried over magnesium sulphate. After removing the solvents, the resulting oily residue is filtered over 10 g of silica gel using cyclohexane. 9.8 g of the purified base are converted with ethereal hydrochloric acid into the hydrochloride and the latter is crystallised from isopropanol/diethyl ether. The resulting 4-hydroxy-1-[2-(6-methoxyindan-1-yl)ethyl]-1,2,5,6-tetrahydro-pyridine- alias 1-[2-(6-methoxyindan-1-yl)ethyl]-4-oxo-piperidine-3-carboxylic acid ethyl ester hydrochloride melts at 140°–145°.

The starting materials are obtained, for example, as follows:

12.8 g (50 mmol) of methanesulphonic acid (6-methoxyindan-1-ylmethyl) ester and 3.7 g (75 mmol) of sodium cyanide are dissolved in 70 ml of dimethyl sulphoxide and heated at 80° for 6 hours. The reaction mixture is poured onto 200 ml of ice-water and extracted three times by shaking with 100 ml of toluene each time. The organic phases are combined, subsequently washed with saturated sodium chloride solution and dried over magnesium sulphate. After removing the solvent in vacuo, crude 2-(6-methoxyindan-1-yl)acetonitrile is obtained.

9.3 g (49 mmol) of crude 2-(6-methoxyindan-1-yl)acetonitrile are dissolved in 100 ml of methanol and, after the addition of 1 g of Raney nickel and 20 g of liquid ammonia, are hydrogenated at 70°–80° and 120 bar pressure. After 3 hours, the catalyst is filtered off from the methanolic solution and is subsequently washed with methanol. The methanolic solutions are combined and rendered acidic with hydrochloric acid. The acidic solution is concentrated to dryness by evaporation in vacuo, and the residue is dissolved in 100 ml of water, rendered alkaline with concentrated sodium hydroxide solution and extracted by shaking with diethyl ether. The ethereal phases are washed with saturated sodium chloride solution and dried over magnesium sulphate. After removing the solvent, crude 2-(6-methoxyindan-1-yl)ethylamine is obtained in the form of a yellow oil.

6.1 g (31.8 mmol) of 2-(6-methoxyindan-1-yl)ethylamine and 10 g (100 mmol) of ethyl acrylate are dissolved in 60 ml of ethanol and maintained under reflux for 12 hours. Subsequently, the solvent is removed in vacuo and the residue is purified on 20 g of Florisil with cyclohexane. Crude N-[2-(6-methoxyindan-1-yl)ethyl]imino-di-(3-propionic acid) diethyl ester is obtained in the form of a yellow, mobile oil.

EXAMPLE 19

11.8 g (32.4 mmol) of N-(6-methoxyindan-1-yl)imino-di-(3-propionic acid) diethyl ester are dissolved in 100 ml of toluene and added dropwise, at room temperature, to a suspension of 2.1 g (42 mmol) of 50% sodium hydride dispersion in 50 ml of toluene. The reaction mixture is heated at 80° for 3 hours. The external temperature is then increased to 110°–120° and a mixture of ethanol and toluene is distilled off. Subsequently, the reaction mixture is cooled, poured onto a mixture of 100 ml of 2N hydrochloric acid and ice and extracted by shaking with diethyl ether, and the acidic aqueous phases are rendered basic with sodium bicarbonate solution. The resulting mixture is extracted by shaking with diethyl ether/ethyl acetate (2:1), and the organic phases are washed with saturated sodium chloride solution and dried over magnesium sulphate. After removing the solvent in vacuo, the residue is purified on silica gel with cyclohexane. 4-hydroxy-1-(6-methoxyindan-1-yl)-1,2,5,6-tetrahydropyridine- alias 1-(6-methoxyindan-1-yl)-4-oxo-piperidine-3-carboxylic acid ethyl ester is obtained in the form of an oil. The latter is converted with ethereal hydrochloric acid into the hydrochloride which is recrystallised from ethanol/diethyl ether. The resulting 4-hydroxy-1-(6-methoxyindan-1-yl)-1,2,5,6-tetrahydro-pyridine- and 1-(6-methoxyindan-1-yl)-4-oxo-piperidine-3-carboxylic acid ethyl ester hydrochloride melts at 170°–173°.

The starting material is obtained, for example, as follows:

9.5 g (50 mmol) of 6-methoxyindane-1-carboxylic acid are dissolved in 100 ml of trichloromethane, and 8.9 g (75 mmol) of thionyl chloride and 3 drops of dimethylformamide are added thereto and the whole is maintained under reflux for 1.5 hours. The reaction mixture is concentrated to dryness by evaporation in vacuo and then 50 ml of toluene are added, the mixture is again concentrated by evaporation, and the procedure is repeated with the addition of a further 50 ml of toluene.

The resulting residue (10.8 g) is dissolved in 200 ml of dichloromethane, 0.32 g (1 mmol) of tetrabutylammonium bromide is added and, at 0°, a solution of 5.0 g (77 mmol) of sodium azide in 70 ml of water is added dropwise and the whole is stirred at 0° for 2 hours. The organic phase is then separated off, the aqueous phases are subsequently washed with dichloromethane and the combined dichloromethane phases are dried at 0° over magnesium sulphate. 11.4 g (100 mmol) of trifluoroacetic acid are added to the combined dichloromethane solutions and the whole is boiled under reflux for 18 hours. When the reaction mixture has cooled, ice is added, and the mixture is extracted by shaking with 100 ml of saturated sodium bicarbonate solution and dried over magnesium sulphate. After removing the solvent, the resulting crystalline residue is crystallised from acetone/cyclohexane/petroleum ether and yields pure N-(6-methoxyindan-1-yl)trifluoroacetamide of m.p. 128°–136°.

19 g (73 mmol) of N-(6-methoxyindan-1-yl)trifluoroacetamide are dissolved in 300 ml of methanol and, at 40°, 100 ml of N potassium hydroxide solution are added dropwise thereto. The strongly alkaline solution is stirred at room temperature for 12 hours, filtered over diatomaceous earth, subsequently washed with water and rendered acidic with concentrated hydrochloric acid. The resulting solution is substantially concentrated in vacuo, and the residue is rendered alkaline with concentrated sodium hydroxide solution and extracted by shaking with diethyl ether. The ethereal solutions are washed with saturated sodium chloride solution, dried over solid potassium hydroxide and concentrated under reduced pressure. Ethereal hydrochloric acid is added to the resulting oily residue and the hydrochloride which precipitates is recrystallised from ethanol/diethyl ether. The resulting N-(6-methoxyindan-1-yl)ammonium chloride melts at 253°–254°.

The base is freed from 6.0 g (30 mmol) of N-(6-methoxyindan-1-yl)ammonium chloride using diethyl ether and 2N sodium hydroxide solution. 5.3 g (30 mmol) of the resulting base are dissolved in 50 ml of ethanol, 9.0 g (90 mmol) of ethyl acrylate are added and the whole is boiled under reflux for 24 hours. The mixture is then left to stand at room temperature for 8 days. The solvent is removed in vacuo and the residue is purified on silica gel with cyclohexane. The resulting eluates are concentrated to dryness by evaporation. N-(5-methoxyindan-1-yl)imino-di-(3-propionic acid) diethyl ester is obtained in the form of an oily residue which is used without further purification.

EXAMPLE 20

4.35 g (90 mmol) of sodium hydride dispersion (50% in oil) are added in portions, while stirring at room temperature, to a solution of 29.32 g (75 mmol) of N-[(7-methoxy-1,2,3,4-tetrahydro-naphth-1-yl)methyl]imino-di-(3-propionic acid) diethyl ester in 200 ml of dimethylformamide. Stirring is then carried out at room temperature for 1 hour. The reaction mixture is concentrated by evaporation under a high vacuum, cold 2N hydrochloric acid is added to the residue and extraction is carried out with diethyl ether. The combined hydrochloric acid extracts are extracted with dichloromethane, and the combined organic phases are dried over sodium sulphate and again concentrated by evaporation. The oily residue is dissolved hot in acetone whereupon, after cooling, 4-hydroxy-1-[(7-methoxy-1,2,3,4-tetrahydro-naphth-1-yl)methyl]-1,2,5,6-tetrahydro-pyridine-alias 1-[(7-methoxy-1,2,3,4-tetrahydro-naphth-1-yl)methyl]-4-oxo-piperidine-3-carboxylic acid ethyl ester hydrochloride of m.p. 132°–134° crystallises out.

The starting material can be manufactured, for example, as follows:

22 g (220 mmol) of ethyl acrylate are added to a solution of 19.1 g (100 mmol) of 1,2,3,4-tetrahydro-7-methoxy-naphth-1-ylmethylamine in 300 ml of ethanol and the whole is stirred at 65° for 48 hours. After cooling, the solvent is evaporated off under reduced pressure to yield N-[(7-methoxy-1,2,3,4-tetrahydro-naphth-1-yl)methyl]imino-di-(3-propionic acid) diethyl ester in the form of a reddish oil.

EXAMPLE 21

2.28 g (60 mmol) of sodium borohydride are added in portions, while stirring at 0°–5°, to a solution of 11.45 g (30 mmol) of 4-hydroxy-1,2,5,6-tetrahydro-1-[(7-methoxy-1,2,3,4-tetrahydro-naphth-1-yl)methyl]-pyridine-3-carboxylic acid ethyl ester hydrochloride in 150 ml of ethanol. After stirring for 1 hour at 0°–5°, the reaction mixture is concentrated under reduced pressure, water is added to the residue and extraction is carried out with dichloromethane. The combined organic phases are washed with water, dried over sodium sulphate and completely concentrated by evaporation. The crude product, 8.0 g of yellow oil, is chromatographed over 320 g of silica gel (0.040–0.063) with a mixture of toluene and ethyl acetate (1:1). In this manner there is obtained a 1:1 mixture of cis- and trans-4-hydroxy-1-[(7-methoxy-1,2,3,4-tetrahydro-naphth-1-yl)methyl]-piperidine-3-carboxylic acid ethyl ester in the form of a colourless oil.

EXAMPLE 22

A solution of 2.06 g (18 mmol) of methanesulphonic acid chloride in 20 ml of toluene is added dropwise, while stirring at 0°–5°, to a solution of 5.2 g (15 mmol) of cis/trans mixture of 4-hydroxy-1-[(7-methoxy-1,2,3,4-tetrahydro-naphth-1-yl)methyl]-piperidine-3-carboxylic acid ethyl ester and 11.4 g (75 mmol) of 1,8-diazabicyclo[5.4.0]undec-7-ene in 100 ml of toluene. The reaction mixture is then allowed to warm to room temperature and is stirred for a further 18 hours at room temperature. Ice-water is added to the reaction mixture and the organic phase is extracted with 2N hydrochloric acid. The combined hydrochloric acid extracts are rendered alkaline with concentrated sodium hydroxide solution and extracted with dichloromethane. The combined organic phases are washed with water, dried over sodium sulphate and concentrated by evaporation. The oily residue (4.85 g) is chromatographed on 240 g of silica gel (0.040–0.063) with toluene/ethyl acetate (9:1) to yield 1-[(7-methoxy-1,2,3,4-tetrahydro-naphth-1-yl)methyl]-1,2,5,6-tetrahydro-pyridine-3-carboxylic acid ethyl ester in the form of a light-yellow oil. The hydrochloride produced with hydrochloric acid in diethyl ether crystallises from ethanol/diethyl ether, m.p. 177°–179° (decomposition).

EXAMPLE 23

0.86 g (18 mmol) of sodium hydride dispersion (50% in oil) are added in two portions, while stirring at room temperature, to a solution of 5.45 g (15 mmol) of N-[(7-methoxy-1,2,3,4-tetrahydro-naphth-2-yl)methyl]imino-di-(3-propionic acid) dimethyl ester in 55 ml of dimethylformamide. After being stirred for 2 hours, the reaction mixture is completely concentrated by evaporation under a high vacuum. Cold 2N hydrochloric acid is added to the resulting residue and extraction is carried out with diethyl ether The aqueous hydrochloric acid extracts are combined and extracted with dichloromethane. The organic phases are combined, dried over sodium sulphate and concentrated by evaporation. The oily residue is dissolved in hot acetone and diethyl ether is added until the mixture becomes turbid, whereupon, upon cooling, 4-hydroxy-1-[(7-methoxy-1,2,3,4-tetrahydro-naphth-2-yl)methyl]-1,2,5,6-tetrahydro-pyridine-3-carboxylic acid methyl ester hydrochloride alias 1-[(7-methoxy-1,2,3,4-tetrahydro-naphth-2-yl)methyl]-4-oxo-piperidine-3-carboxylic acid methyl ester hydrochloride of m.p. 167°-169° crystallises out.

The starting material can be manufactured, for example, in the following manner:

A solution of 23.43 g (100 mmol) of 7-methoxy-1,2,3,4-tetrahydro-naphthalene-2-carboxylic acid ethyl ester in 160 ml of absolute tetrahydrofuran is added dropwise, over a period of 30 minutes, while stirring at room temperature, to a suspension of 3.79 g (100 mmol) of lithium aluminium hydride in 160 ml of absolute diethyl ether. After stirring at room temperature for 1 hour, 3.8 ml of water, 3.8 ml of sodium hydroxide solution (15%) and 11.4 ml of water are added to the reaction mixture. The resulting precipitate is filtered off with suction and the filtrate is concentrated to dryness by evaporation in vacuo. The oily residue is dissolved in diethyl ether, washed with water, dried with sodium sulphate and concentrated to dryness by evaporation. 7-methoxy-1,2,3,4-tetrahydro-naphthalene-2-methanol is obtained in the form of a yellow oil.

20.96 g (110 mmol) of p-toluenesulphonic acid chloride are added at room temperature, while stirring, to a solution of 19.2 g (100 mmol) of 7-methoxy-1,2,3,4-tetrahydro-naphthalene-2-methanol in 80 ml of absolute pyridine, the slightly exothermic reaction being maintained at room temperature with an ice bath. The reaction mixture is stirred at room temperature for 1 hour to complete the reaction and is then diluted with ice-water and extracted with diethyl ether. The organic phase is washed while ice-cold with 2N hydrochloric acid and water, is dried over sodium sulphate, filtered and concentrated by evaporation under reduced pressure. The resulting oil is crystallised from diethyl ether/pentane to yield p-toluenesulphonic acid (7-methoxy-1,2,3,4-tetrahydro-naphth-2-ylmethyl) ester of m.p. 64°-66°.

A solution of 3.9 g of sodium azide in 10 ml of water is added to a solution of 13.86 g (40 mmol) of p-toluenesulphonic acid (7-methoxy-1,2,3,4-tetrahydro-naphth-2-ylmethyl) ester in 200 ml of ethanol and the whole is boiled under reflux for 18 hours. After cooling, the alcohol is evaporated off under reduced pressure, water is added to the residue and extraction is carried out with dichloromethane. The organic phase is washed with water, dried over sodium sulphate and concentrated by evaporation. (7-methoxy-1,2,3,4-tetrahydro-naphth-2-yl)methylazide is obtained in the form of a yellow oil.

A solution of 6.51 g (30 mmol) of (7-methoxy1,2,3,4-tetrahydro-naphth-2-yl)methylazide in 100 ml of absolute tetrahydrofuran is added dropwise, over a period of 30 minutes, at room temperature, to a stirred suspension of 1.14 g (30 mmol) of lithium aluminium hydride in 100 ml of absolute diethyl ether. After stirring at room temperature for 2 hours, the reaction mixture is hydrolysed with 1.14 ml of water, 1.14 ml of sodium hydroxide solution (15%) and 3.4 ml of water. The resulting precipitate is filtered off with suction and the filtrate is concentrated by evaporation under reduced pressure. The resulting oil is dissolved in diethyl ether and taken up in 2N hydrochloric acid. The combined hydrochloric acid extracts are rendered alkaline with concentrated sodium hydroxide solution while cooling with ice and extracted with dichloromethane. The organic phases are combined, dried over sodium sulphate and concentrated by evaporation under reduced pressure. 7-methoxy-1,2,3,4-tetrahydro-naphth-2-ylmethylamine is obtained in the form of a yellow oil, m.p. of the hydrochloride 205°-206°.

3.78 g of methyl acrylate are added to a solution of 3.82 g (20 mmol) of 7-methoxy-1,2,3,4-tetrahydro-naphth-2-ylmethylamine in 60 ml of methanol and the whole is stirred at 65° for 18 hours. After cooling, the reaction mixture is concentrated by evaporation under reduced pressure. N-[(7-methoxy-1,2,3,4-tetrahydro-naphth-2-yl)methyl]imino-di-(3-propionic acid) dimethyl ester is obtained in the form of a reddish oil.

EXAMPLE 24

To a solution of 5.19 g (15 mmol) of p-toluene-sulphonic acid (7-methoxy-1,2,3,4-tetrahydro-naphth-2-ylmethyl) ester in 75 ml of dimethylformamide there are added first 3.66 g (16.5 mmol) of 1,2,5,6-tetrahydropyridine-3-carboxylic acid methyl ester hydrobromide (guvacoline hydrobromide) and then 6.78 g (52.5 mmol) of N-ethyl-N,N-diisopropylamine. The mixture is stirred at 60° for 18 hours and then concentrated by evaporation under a high vacuum. Water is added to the residue and extraction is carried out with diethyl ether. The organic phases are washed with water and extracted with 2N hydrochloric acid. The hydrochloric acid extracts are rendered alkaline at reduced temperature with sodium hydroxide solution (30%) and are extracted with dichloromethane, whereupon the combined organic phases are dried over sodium sulphate and concentrated by evaporation under reduced pressure. 1-[(7-methoxy-1,2,3,4-tetrahydro-naphth-2-yl)methyl]-1,2,5,6-tetrahydropyridine-3-carboxylic acid methyl ester is obtained in the form of a light-yellow oil.

The hydrochloride produced with hydrochloric acid in diethyl ether crystallises from acetone/diethyl ether with m.p. 161°-163°.

EXAMPLE 25

17.4 ml of n-butyllithium in hexane are added at 0°-5° to a solution of 2.81 g of diisopropylamine in 30 ml of dry tetrahydrofuran. The whole is stirred at room temperature for 30 minutes, is again cooled to −15° and a solution of 6.13 g (25 mmol) of 1-[(5-methoxybenzocyclobuten-1-yl)methyl]-piperidin-4-one in 30 ml of tetrahydrofuran is added. After 15 minutes, a solution of 3.05 g (28 mmol) of trimethylchlorosilane in 15 ml of tetrahydrofuran is added dropwise. The whole is stirred overnight at room temperature, filtered and concentrated to dryness by evaporation in vacuo. 1-[(5-methoxybenzocyclobuten-1-yl)methyl]-4-trimethylsilyloxy-1,2,5,6-tetrahydro-pyridine is thus obtained in the form of a light-yellow oil.

6.39 g (20 mmol) of 1-[(5-methoxybenzocyclobuten-1-yl)methyl]-4-trimethylsilyloxy-1,2,5,6-tetrahydropyridine dissolved in 50 ml of dichloromethane are added dropwise to a solution, cooled to 0°, of 2.3 g (24 mmol) of chloroformic acid ethyl ester and 60 mg (2.4 mmol) of anhydrous zinc bromide in 50 ml of dry dichloromethane. After heating to room temperature, stirring is then carried out for 1 hour, whereupon the mixture is poured onto 150 ml of saturated sodium bicarbonate solution and extracted with dichloromethane. The combined organic phases are dried over sodium sulphate and concentrated by evaporation. The residue is dissolved in 70 ml of ethanol and acidified with ethanolic hydrochloric acid solution. After adding diethyl ether and cooling, 4-hydroxy-1-[(5-methoxybenzocyclobuten-1-yl)methyl]-1,2,5,6-tetrahydro-pyridine-3- carboxylic acid ethyl ester hydrochloride alias 1-[(5-methoxybenzocyclobuten-1-yl)methyl]-4-oxo-piperidine-3-carboxylic acid ethyl ester hydrochloride of m.p. 181°–182° crystallises out.

The starting material can be manufactured, for example, as follows:

To a solution of 12.11 g (50 mmol) of methanesulphonic acid (5-methoxybenzocyclobuten-1-ylmethyl) ester in 100 ml of dimethylformamide there are added first 8.45 g (55 mmol) of piperidone hydrochloride monohydrate and then 22.62 g (175 mmol) of N-ethyl-N,N-diisopropylamine. The mixture is stirred at 80° C. for 18 hours and, after cooling, is concentrated to dryness by evaporation under reduced pressure. The residue is dissolved in diethyl ether and washed with water. The organic phase is separated off and extracted with 2N hydrochloric acid. The hydrochloric acid extracts are combined, rendered alkaline at reduced temperature with sodium hydroxide solution and extracted with dichloromethane. The extracts are combined, dried over sodium sulphate and concentrated to dryness by evaporation under reduced pressure. A dark brown resin is obtained which is purified by chromatography on 350 g of silica gel (0.040–0.063 mm) with toluene-/ethyl acetate (1:1). 1-[(5-methoxybenzocyclobuten-1-yl)methyl]piperidin-4-one is obtained in the form of a light-yellow oil.

The hydrochloride produced with hydrochloric acid in diethyl ether crystallises from acetone/diethyl ether with m.p. 162°–163°.

EXAMPLE 26

1.73 g (36 mmol) of sodium hydride are introduced over a period of 30 minutes, while stirring, at room temperature, into a solution of 10.48 g (30 mmol) of N-(7-methoxy-1,2,3,4-tetrahydro-naphth-2-yl)imino-di-3-propionic acid) dimethyl ester in 100 ml of absolute dimethylformamide. The reaction mixture is stirred at room temperature for 2 hours to complete the reaction and is concentrated to dryness by evaporation under reduced pressure. Cold 2N hydrochloric acid is added to the residue and extraction is carried out with diethyl ether. The combined aqueous-hydrochloric acid extracts are extracted with dichloromethane and the combined dichloromethane extracts are dried over sodium sulphate and concentrated by evaporation. The oily residue is dissolved hot in acetonitrile and diethyl ether is added until the mixture becomes turbid, whereupon, on cooling, 4-hydroxy-1-(7-methoxy-1,2,3,4-tetrahydro-naphth-2-yl)1,2,5,6-tetrahydro-pyridine- alias 1-(7-methoxy-1,2,3,4-tetrahydro-naphth-2-yl)-4-oxo-piperidine-3-carboxylic acid methyl ester hydrochloride of m.p. 188°–190° (decomposition) crystallises out.

The starting material can be manufactured, for example, in the following manner:

4.73 g (55 mmol) of methyl acrylate are added to a solution of 4.43 g (25 mmol) of 1,2,3,4-tetrahydro-7-methoxy-naphth-2-ylamine in 150 ml of methanol and the whole is heated under reflux for 24 hours. A further 4.73 g (55 mmol) of methyl acrylate are then added and heating under reflux is carried out for a further 48 hours. After cooling, the reaction mixture is concentrated by evaporation to yield N-(7-methoxy-1,2,3,4-tetrahydro-naphth-2-yl)imino-di-3-propionic acid) dimethyl ester in the form of a reddish oil.

EXAMPLE 27

3-(7-methoxy-1,2,3,4-tetrahydro-naphth-2-ylamino)-propionic acid methyl ester, m.p. of the hydrochloride 187°–188° (decomposition), and 3-(7-methoxy-1,2,3,4-tetrahydro-naphth-2-ylamino)propionic acid ethyl ester, m.p. of the hydrochloride 191°–192°, can be manufactured in a manner analogous to that described in Example 26 by reacting with an equimolar amount of methyl acrylate and ethyl acrylate, respectively.

EXAMPLE 28

1.14 g (30 mmol) of sodium borohydride are added in portions, while stirring at 0°–5°, to a suspension of 5.3 g (15 mmol) of 4-hydroxy-1-(7-methoxy-1,2,3,4-tetrahydro-naphth-2-yl)-1,2,5,6-tetrahydro-pyridine-3-carboxylic acid methyl ester hydrochloride in 75 ml of methanol. The reaction mixture is stirred at 0°–5° for 1 hour to complete the reaction and is concentrated under reduced pressure. Water is added to the reaction mixture and extraction is carried out with dichloromethane. The combined organic phases are washed with water, dried over sodium sulphate and concentrated by evaporation. A mixture of cis- and trans-4-hydroxy-1-(7-methoxy-1,2,3,4-tetrahydro-naphth-2-yl)-piperidine-3-carboxylic acid methyl ester is obtained in the form of a yellow oil.

EXAMPLE 29

A solution of 1.78 g (15.5 mmol) of methanesulphonic acid chloride in 15 ml of toluene is added dropwise, while stirring at 0°–5°, to a solution of 4.15 g (13 mmol) of the mixture of cis- and trans-4-hydroxy-1-(7-methoxy-1,2,3,4-tetrahydro-naphth-2-yl)-piperidine-3-carboxylic acid methyl ester and 9.89 g (65 mmol) of 1,8-diazabicyclo[5.4.0]undec-7-ene in 90 ml of toluene. The reaction mixture is then allowed to warm to room temperature and is stirred for a further 18 hours. Ice-water is then added to the reaction mixture and the organic phase is extracted with 2N hydrochloric acid. The combined hydrochloric acid extracts are rendered alkaline with concentrated sodium hydroxide solution and repeatedly extracted with dichloromethane. The combined extracts are washed with water, dried over sodium sulphate and concentrated by evaporation. The resulting crude product is purified by chromatography on 190 g of silica gel (0.040–0.063) using toluene/ethyl acetate (1:1). 1-(7-methoxy-1,2,3,4-tetrahydro-naphth-2-yl)-1,2,5,6-tetrahydropyridine-3-carboxylic acid methyl ester is obtained in the form of a yellow oil which crystallises from diethyl ether/pentane; m.p. 65°–66°. The hydrochloride produced with hydrochloric acid in diethyl ether crystallises from acetone/diethyl ether with m.p. 210°–212° (decomposition).

EXAMPLE 30

7.7 g (26 mmol) of methanesulphonic acid [2-(6-methoxyindan-1-yl)ethyl] ester are dissolved in 20 ml of toluene and added at room temperature to a solution of 6.3 g (28.6 mmol) of guvacoline hydrobromide and 12.7 g (57 mmol) of N-ethyl-N,N-diisopropylamine in 15 ml of dimethylformamide. The mixture is left to stand at room temperature for 3 days and is then freed of solvent at 40°–50° under reduced pressure.

The resulting residue is dissolved in 2N hydrochloric acid and extracted by shaking with diethyl ether, and the acidic aqueous solution is rendered basic with sodium bicarbonate while cooling with ice. The resulting mixture is extracted by shaking with diethyl ether, and the ethereal phases are washed with saturated sodium chloride solution and dried over magnesium sulphate. The resulting 1-[2-(6-methoxyindan-1-yl)ethyl]-1,2,5,6-tetrahydro-pyridine-3-carboxylic acid methyl ester is purified by chromatography on 6 g of silica gel with cyclohexane and yields a yellow oil.

The crude base is converted with ethereal hydrochloric acid into the hydrochloride and the latter is recrystallised from isopropanol/diethyl ether. 1-[2-(6-methoxyindan-1-yl)ethyl]-1,2,5,6-tetrahydropyridine-3-carboxylic acid methyl ester hydrochloride is obtained which melts at 145°–148°.

The starting materials are obtained, for example, as follows:

15.7 g (76 mmol) of 6-methoxyindan-1-ylacetic acid are dissolved in 150 ml of tetrahydrofuran. Then, while stirring at 40°–50°, diborane, which has been produced by adding 21.6 g (152 mmol) of boron trifluoride etherate dropwise to a suspension of 4.3 g (114 mmol) of sodium borohydride in 60 ml of diethylene glycol at 40°–60° while stirring, is introduced with a stream of nitrogen. When the diborane production has ceased (approximately 1 hour), the reaction solution is maintained under reflux for 8 hours, is cooled with an ice bath and 140 ml of a 1 molar sodium dihydrogen phosphate solution are slowly added thereto.

The mixture is concentrated under reduced pressure, rendered alkaline with 50 ml of 2N sodium hydroxide solution and extracted by shaking with diethyl ether. The ethereal solutions are washed with saturated sodium chloride solution and dried over magnesium sulphate. Removal of the solvent yields crude 2-(6-methoxyindan-1-yl)ethanol in the form of a yellowish viscous oil.

5.0 g (26.0 mmol) of crude 2-(6-methoxyindan-1-yl)ethanol are dissolved in 50 ml of dichloromethane and, while cooling with ice, 3.6 g (31 mmol) of methanesulphonic acid chloride and 3.1 g (31 mmol) of triethylamine are added dropwise. The mixture is stirred at room temperature for 3 hours, the triethyl-ammonium chloride which has precipitated is filtered off and the filtrate is extracted by shaking with ice-water. The organic phases are washed with saturated sodium chloride solution, dried over magnesium sulphate and concentrated by evaporation at 40° under reduced pressure. Methanesulphonic acid 2-(6-methoxyindan-1-yl)ethyl ester is obtained which can be used without further purification.

EXAMPLE 31

1.5 ml of concentrated hydrochloric acid is added to a solution of 4.05 g (15 mmol) of 4-hydroxy-1-[(5-methoxybenzocyclobuten-1-yl)methyl]-1,2,5,6-tetrahydropyridine-3-carboxylic acid nitrile hydrochloride in 100 ml of 95% ethanol and the whole is heated under reflux for 15 hours. After cooling, the whole is concentrated to approximately 30 ml under reduced pressure and this solution is poured into a mixture of 5N hydrochloric acid and 20 ml of toluene, whereupon, on stirring and cooling, 4-hydroxy-1-[(5-methoxybenzocyclobuten-1-yl)methyl]-1,2,5,6-tetrahydro-pyridine-3-carboxylic acid ethyl ester hydrochloride alias 1-[(5-methoxybenzocyclobuten-1-yl)methyl]-4-oxo-piperidine-3-carboxylic acid ethyl ester hydrochloride of m.p. 181°–182° C. crystallises out.

The starting material can be manufactured, for example, in the following manner:

10.5 g (0.1 mol) of triethylamine and 5.84 g (0.11 mol) of acrylonitrile are added to 30.16 g (0.1 mol) of 3-(5-methoxybenzocyclobuten-1-ylmethylamino)-propionic acid ethyl ester in 250 ml of ethanol and the whole is stirred at room temperature for 15 hours. The reaction mixture is then concentrated under a water-jet vacuum, and the residue is taken up in diethyl ether and washed neutral with ice-water. The ethereal solution is dried over potassium carbonate, filtered and concentrated by evaporation; 3-{N-(2-cyanoethyl)-N-[(5-methoxybenzocyclobuten-1-yl)methyl]-amino}propionic acid ethyl ester is obtained in the form of a yellow oil.

A solution of 13.07 g (41.3 mmol) of 3-{N-(2-cyanoethyl)-N-[(5-methoxybenzocyclobuten-1-yl)methyl]-amino}propionic acid ethyl ester in 200 ml of tetrahydrofuran is added dropwise under a nitrogen atmosphere to a suspension of 5.73 g of sodium hydride (approximately 55% in mineral oil) in 100 ml of tetrahydrofuran and the whole is stirred at room temperature for 16 hours After the addition of 70 ml of 2N sulphuric acid, a yellow solution is obtained. To this are added 300 ml of diethyl ether and 100 ml of water, 2 layers being produced The aqueous layer is extracted three times with 100 ml of diethyl ether each time. The combined organic phases are dried over sodium sulphate, concentrated to approximately 100 ml under reduced pressure and poured into a mixture of 80 ml of 5N hydrochloric acid and 20 ml of toluene, whereupon, on stirring and cooling, 4-hydroxy-1-[(5-methoxybenzocyclobuten-1-yl)methyl]-1,2,5,6-tetrahydro-pyridine-3-carboxylic acid nitrile hydrochloride and 1-[(5-methoxybenzocyclobuten-1-yl)-methyl]-4-oxo-piperidine-3-carboxylic acid nitrile hydrochloride crystallise out.

EXAMPLE 32

4 ml of concentrated sulphuric acid are added to a solution of 10.2 g (0.04 mol) of 1-[(5-methoxybenzocyclobuten-1-yl)methyl]-1,2,5,6-tetrahydro-pyridine-3-carboxylic acid nitrile in 200 ml of 96% ethanol and the whole is heated under reflux for 16 hours. After cooling, the reaction mixture is concentrated to 50 ml under reduced pressure, and the residue is partitioned between 200 ml of dichloromethane and 100 ml of water and neutralised with saturated sodium bicarbonate solution. The organic phase is separated off and the aqueous phase is re-extracted once more by shaking with 100 ml of dichloromethane. The combined organic phases are dried over sodium sulphate, filtered and concentrated by evaporation. The crude product is purified by chromatography on 250 g of silica gel, converted into the hydrochloride with ethanolic hydrochloric acid and crystallised from ethanol/diethyl ether. 1-[(5-methoxybenzocyclobuten-1-yl)methyl]-1,2,5,6-tetrahydro-pyridine-3-carboxylic acid ethyl ester hydrochloride of m.p. 204.5°–205.5° is obtained.

The starting material can be manufactured, for example, in the following manner:

42.2 g (0.1 mol) of methanesulphonic acid (5-methoxybenzocyclobuten-1-ylmethyl) ester, 11.9 g (0.11 mol) of 1,2,5,6-tetrahydropyridine-3-carboxylic acid nitrile and 15 g of N-ethyl-N,N-diisopropylamine are dissolved under nitrogen in 250 ml of dimethylformamide and the whole is stirred for 16 hours. The reaction mixture is concentrated to approximately 100 ml under reduced pressure, 300 ml of water are added thereto and extraction is carried out three times by shaking with 150 ml of dichloromethane each time. The combined organic phases are dried over sodium sulphate, filtered and concentrated by evaporation. The residue is purified by chromatography on 500 g of silica gel with toluene/ethyl acetate (19:1) as eluant. 1-[(5-methoxybenzocyclobuten-1-yl)methyl]-1,2,5,6-tetrahydropyridine-3-carboxylic acid nitrile is obtained in the form of a yellow oil.

EXAMPLE 33

A solution of 19.1 g (50 mmol) of a mixture of cis- and trans-4-bromo-1-[(5-methoxybenzocyclobuten-1-yl)methyl]-piperidine-3-carboxylic acid ethyl ester and 8.2 g (0.1 mol) of anhydrous sodium acetate in 100 ml of glacial acetic acid is heated under reflux for 16 hours. After cooling, the reaction mixture is concentrated under reduced pressure, partitioned between dichloromethane and aqueous sodium carbonate solution, the combined organic phases are dried over sodium sulphate and concentration by evaporation is carried out. The resulting oily mixture of cis- and trans-4-acetoxy-1-[(5-methoxybenzocyclobuten-1-yl)methyl]-piperidine-3-carboxylic acid ethyl ester is purified by chromatography on 600 g of silica gel (60, Merck) with trichloromethane/methanol (98:2) as eluant. The trans-isomer is isolated first, then the cis-isomer. The hydrochloride is prepared from the latter with ethereal hydrochloric acid solution. Its melting point is 202°–203° C.

The starting material can be manufactured, for example, in the following manner:

While stirring, 30.14 g (0.1 mol) of 1-[(5-methoxybenzocyclobuten-1-yl)methyl]-1,2,5,6-tetrahydropyridine-3-carboxylic acid ethyl ester are introduced in portions into 150 ml of a 33% solution of hydrogen bromide in glacial acetic acid. After stirring at room temperature for 18 hours, the reaction mixture is concentrated under reduced pressure and partitioned between dichloromethane and aqueous sodium carbonate solution. The organic phase is dried over sodium sulphate and the solvent is evaporated off under reduced pressure. A mixture of cis- and trans-4-bromo-1-[(5-methoxybenzocyclobuten-1-yl)methyl]-piperidine-3-carboxylic acid ethyl ester is obtained in the form of a yellow oil.

EXAMPLE 34

A solution of 11 g (0.1 mol) of benzyl alcohol in 100 ml of tetrahydrofuran is added to a suspension of 4.8 g of sodium hydride (50% suspension in mineral oil) in 100 ml of dry tetrahydrofuran and, when the gas reaction has ceased, the reaction mixture is heated to reflux. After cooling, a solution of 30.14 g (0.1 mol) of 1-[(5-methoxybenzocyclobuten-1-yl)methyl]-1,2,5,6-tetrahydro-pyridine-3-carboxylic acid ethyl ester in 200 ml of tetrahydrofuran is added dropwise thereto and the whole is again heated under reflux for 5 hours. After cooling, the solvent is concentrated by evaporation. A mixture of cis- and trans-4-benzyloxy-1-[(5-methoxybenzocyclobuten-1-yl)methyl]-piperidine-3-carboxylic acid ethyl ester is obtained in the form of an oil.

EXAMPLE 35

10.24 g (25 mmol) of a mixture of cis- and trans-4-benzyloxy-1-[(5-methoxybenzocyclobuten-1-yl)methyl]-piperidine-3-carboxylic acid ethyl ester are dissolved in 150 ml of 95% ethanol, 2 g of 10% palladium-on-carbon are added and hydrogenation is carried out in a Parr apparatus for 12 hours at room temperature. The reaction mixture is filtered over diatomaceous earth and concentrated to dryness by evaporation. The evaporation residue is chromatographed on 400 g of silica gel with toluene/ethyl acetate (19:1) as eluant. First trans-4-hydroxy-1-[(5-methoxybenzocyclobuten-1-yl)methyl]-piperidine-3-carboxylic acid ethyl ester is isolated and then cis-4-hydroxy-1-[(5-methoxybenzocyclobuten-1-yl)methyl]-piperidine-3-carboxylic acid ethyl ester (m.p. of the hydrochloride: 156°–160°).

EXAMPLE 36

3.3 g of sodium borohydride are introduced, over a period of 30 minutes, at 0° under a nitrogen atmosphere, into a solution of 25.68 g (50 mmol) of 1-[(5-methoxybenzocyclobuten-1-yl)methyl]-4-ethoxy-3-ethoxycarbonylpyridinium tosylate in 250 ml of 96% ethanol. After stirring for 1 hour at 0° and for 2 hours at room temperature, the solution is concentrated by evaporation under reduced pressure, 70 ml of water are added to the residue and extraction is carried out three times with 100 ml of dichloromethane each time. The organic phases are combined, dried over magnesium sulphate and concentrated by evaporation. A mixture of 80 ml of 5N hydrochloric acid and 20 ml of toluene is added to the residue whereupon, upon stirring and cooling, 4-hydroxy-1-[(5-methoxybenzocyclobuten-1-yl)methyl]-1,2,4,5-tetrahydro-pyridine-3-carboxylic acid ethyl ester hydrochloride alias 1-[(5-methoxybenzocyclobuten-1-yl)methyl]-4-oxo-piperidine-3-carboxylic acid ethyl ester hydrochloride of m.p. 181°–182° C. crystallises out.

The starting material can be manufactured, for example, in the following manner:

19.52 g of 4-ethoxynicotinic acid ethyl ester are added to a solution of 31.84 g (0.1 mol) of p-toluenesulphonic acid (5-methoxybenzocyclobuten-1-yl)methyl ester in 150 ml of 95% ethanol and the whole is stirred for 3 days at room temperature. After distilling off the solvent under reduced pressure, 1-[(5-methoxybenzocyclobuten-1-yl)methyl]-3-ethoxycarbonyl-4-ethoxypyridinium tosylate is obtained in the form of a light-yellow foam.

EXAMPLE 37

A solution of 12.78 g (40 mmol) of 3-[N-(5-methoxybenzocyclobuten-1-ylmethyl)-N-(3-oxopropyl)-amino]-propionic acid ethyl ester in 100 ml of dimethylformamide is added to a solution of 2.43 g (45 mmol) of sodium methoxide in 15 ml of dimethylformamide and the whole is stirred for 3 hours at 40° C. The solvent is then evaporated off under reduced pressure and the residue is separated into its components by chromatography on 400 g of silica gel with dichloromethane/methanol (95:5). Trans-4-hydroxy-1-[(5-methoxybenzocyclobuten-1-yl)methyl]-piperidine-3-carboxylic acid ethyl ester is isolated first and then cis-4-hydroxy-1-[(5-methoxybenzocyclobuten-1-yl)methyl]-piperidine-3-carboxylic acid ethyl ester the hydrochloride of which has a melting point of 156°–160° C.

The starting material can be manufactured, for example, in the following manner:

30.16 g (0.1 mol) of 3-(5-methoxybenzocyclobuten-1-ylmethylamino)propionic acid ethyl ester hydrochloride are stirred in 250 ml of dioxan with 10.5 g (0.1 mol) of triethylamine and 20 g (0.11 mol) of 2-(2-bromoethyl)-1,3-dioxolan for 20 hours at 80°. After cooling, the solvent is evaporated off under reduced pressure, and the residue is taken up in diethyl ether and washed neutral with ice-water. The ethereal solution is dried over potassium carbonate and concentrated by evaporation, whereupon 3-[N-(1,3-dioxolan-2-yl)-N-(5-methoxybenzocyclobuten-1-ylmethyl)amino]propionic acid ethyl ester is isolated in the form of a yellow oil.

200 g of silica gel which has been impregnated with 10% aqueous oxalic acid solution according to J. M. Conia et al.: Synthesis 1978, 63 is added to a solution of 21.8 g (60 mmol) of the compound obtained above in 300 ml of dichloromethane and the suspension is stirred at room temperature for 3 hours. After filtering, washing is carried out with 5% aqueous sodium bicarbonate solution, and the organic phase is dried with sodium sulphate and concentrated by evaporation under reduced pressure. For purification, the evaporation residue is chromatographed on 600 g of silica gel with toluene/ethyl acetate (19:1) as eluant. 3-[N-(5-methoxybenzocyclobuten-1-ylmethyl)N-(3-oxopropyl)-amino]propionic acid ethyl ester is obtained in the form of a yellow oil.

EXAMPLE 38

2 g (5.7 mmol) of 4-hydroxy-1-[(5-methoxybenzocyclobuten-1-yl)methyl]-1,2,5,6-tetrahydro-pyridine-3-carboxylic acid ethyl ester hydrochloride are introduced, at −80° C. under argon, into 80 ml of dichloromethane. While stirring, 1.08 ml (11.3 mmol) of boron tribromide are metered in. After 30 minutes at −80° C., the reaction mixture is gradually heated to +5° C. over a period of 2 hours while stirring. 40 ml of ethanol are then cautiously added and the whole is subsequently concentrated under a water-jet vacuum. The residue is dissolved in 150 ml of ethanol and again concentrated by evaporation under a water-jet vacuum. This procedure is repeated twice more. The resulting residue is then crystallised from ethanol/diethyl ether. 4-hydroxy-1-[(5-hydroxybenzocyclobuten-1-yl)methyl]-1,2,5,6-tetrahydro-pyridine-3-carboxylic acid ethyl ester hydrobromide and 1-[(5-hydroxybenzocyclobuten-1-yl)methyl]-4-oxo-piperidine-3-carboxylic acid ethyl ester hydrobromide of m.p. 192°–194° C. are obtained.

EXAMPLE 39

4-hydroxy-1-[(benzocyclobuten-1-yl)methyl]-1,2,5,6-tetrahydro-pyridine-3-carboxylic acid ethyl ester hydrochloride and 1-[(benzocyclobuten-1-yl)methyl]-4-oxopiperidine-3-carboxylic acid ethyl ester hydrochloride of m.p. 182°–183° C. can be manufactured analogously to Example 1 from 24 g (72 mmol) of N-(benzocyclobuten-1-ylmethyl)imino-di-(3-propionic acid) diethyl ester and 4.7 g (94 mmol) of sodium hydride (50% dispersion in mineral oil) in 650 ml of toluene.

The starting material, N-[(benzocyclobuten-1-yl)methyl]imino-di-(3-propionic acid) diethyl ester (m.p. of hydrochloride 87°–89°) can be manufactured in a manner analogous to that described in Example 1 from 15 g (114 mmol) of benzocyclobuten-1-ylmethylamine and 37 ml (340 mmol) of ethyl acrylate in 200 ml of ethanol.

EXAMPLE 40

4-hydroxy-[(5-methoxy-1-methyl-benzocyclobuten-1-yl)methyl]-1,2,5,6-tetrahydro-pyridine-3-carboxylic acid ethyl ester hydrochloride and 1-[(5-methoxy-1-methyl-benzocyclobuten-1-yl)methyl]-4-oxo-piperidine3-carboxylic acid ethyl ester hydrochloride of m.p. 108° C. can be manufactured analogously to Example 1 from 1.9 g (39 mmol) of sodium hydride (50% dispersion in mineral oil) and 11 g (30 mmol) of N-(5-methoxy-1-methyl-benzocyclobuten-1-ylmethyl)-imino-di-(3-propionic acid) diethyl ester hydrochloride in 280 ml of toluene.

N-(5-methoxy-1-methyl-benzocyclobuten-1-ylmethyl)imino-di-(3-propionic acid) diethyl ester hydrochloride of m.p. 122°–125° can be obtained in a manner analogous to that described in Example 1 from 10 g (56 mmol) of 5-methoxy-1-methyl-benzocyclobuten-1-ylmethylamine and 18 ml (169 mmol) of ethyl acrylate in 100 ml of ethanol The starting material can be obtained, for example, in the following manner:

5 g (29 mmol) of 5-methoxy-1-methyl-benzocyclobutene-1-carboxylic acid nitrile are dissolved in 50 ml of ethanol, and 5 g (290 mmol) of liquid ammonia and 1 g of Raney nickel are added thereto. The reaction mixture is then hydrogenated at 90° C. and $10^7$ Pa for 1 hour. The cooled reaction mixture is filtered over diatomaceous earth and concentrated to dryness by evaporation. The residue is taken up in ethanol, converted into the hydrochloride with hydrochloric acid and crystallised by adding diethyl ether. There is thus obtained 5-methoxy-1-methyl-benzocyclobuten-1-ylmethylammonium chloride of m.p. 159°–160° C.

EXAMPLE 41

Cis-4-hydroxy-1-[(benzocyclobuten-1-yl)methyl]-piperidine-3-carboxylic acid ethyl ester hydrochloride of m.p. 147°–148° is obtained analogously to Example 3 by hydrogenating 3.2 g (10 mmol) of 4-hydroxy-1-[(benzocyclobuten-1-yl)methyl]-1,2,5,6-tetrahydro-pyridine-3-carboxylic acid ethyl ester hydrochloride at $4 \cdot 10^5$ Pa with the addition of 400 mg of platinum oxide in 100 ml of ethanol.

EXAMPLE 42

4-hydroxy-1-(benzocyclobuten-1-yl)-1,2,5,6-tetrahydro-pyridine-3-carboxylic acid ethyl ester hydrochloride alias 1-(benzocyclobuten-1-yl)-4-oxopiperidine-3-carboxylic acid ethyl ester hydrochloride of m.p. 208°–209° C. can be manufactured analogously to Example 1 from 5.9 g (16 mmol) of N-(benzocyclobuten-1-yl)imino-di-(3-propionic acid) diethyl ester and 1 g of a 50% suspension of sodium hydride in toluene.

The starting material, N-(benzocyclobuten-1-yl)imino-di-(3-propionic acid) diethyl ester, can be manufactured in a manner analogous to that described in Example 1, Rf=0.3, hexane/ethyl acetate (4:1), starting from 3.5 g (29 mmol) of benzocyclobuten-1-yl-amine and 9.6 ml (88 mmol) of ethyl acrylate in 100 ml of ethanol.

EXAMPLE 43

2 g (5.6 mmol) of cis-4-hydroxy-1-[(5-methoxybenzocyclobuten-1-yl)methyl]-piperidine-3-carboxylic acid ethyl ester hydrochloride and 20 ml of acetic anhydride are heated under reflux in 100 ml of toluene for 18 hours. 200 ml of ice-water are then added to the cooled reaction mixture and the whole is stirred for 30 minutes. The reaction mixture is rendered alkaline to pH 10 with 2N sodium hydroxide solution and the toluene phase is then separated off. The aqueous phase is extracted twice with dichloromethane. The organic phases are combined, dried over sodium sulphate and concentrated by evaporation. The crude product so obtained is purified by chromatography over the 10-fold amount of silica gel with diethyl ether as eluant. The purified product is converted into the hydrochloride and crystallised from ethanol/diethyl ether. Cis-4-acetoxy-1-[(5-methoxybenzocyclobuten-1-yl)methyl]-piperidine-3-carboxylic acid ethyl ester hydrochloride of m.p. 202°–203° is obtained.

EXAMPLE 44

1-[(benzocyclobuten-1-yl)methyl]-1,2,5,6-tetrahydro-pyridine-3-carboxylic acid ethyl ester hydrochloride of m.p. 157°–158° can be manufactured analogously to Example 5 from 9.2 g (32 mmol) of cis-4-hydroxy-1-[(benzocyclobuten-1-yl)methyl]-piperidine-3-carboxylic acid ethyl ester, 9 ml (64 mmol) of triethylamine, 4.3 g (35 mmol) of 4-dimethylaminopyridine and 2.7 ml (35 mmol) of methanesulphonic acid chloride in 100 ml of dichloromethane, with subsequent treatment with 10 g of potassium hydroxide in 140 ml of ethanol at room temperature.

EXAMPLE 45

3.8 g (13 mmol) of trans-4-hydroxy-1-[(benzocyclobuten-1-yl)methyl]-piperidine-3-carboxylic acid ethyl ester, 3.6 ml (26 mmol) of triethylamine and 1.8 g (14 mmol) of 4-dimethylaminopyridine are introduced into 100 ml of dichloromethane. 1.1 ml of methanesulphonic acid chloride are added thereto at room temperature. Stirring is then carried out for 30 hours, and the reaction mixture is diluted with dichloromethane, washed 3 times with water and dried over sodium sulphate. The crude product is purified by chromatography on silica gel. The purified product is converted into the hydrochloride with ethanolic hydrochloric acid and crystallised by adding diethyl ether. Trans-1-[(benzocyclobuten-1-yl)methyl]-4-methanesulphonyloxypiperidine-3-carboxylic acid ethyl ester hydrochloride of m.p. 145°–146° C. is obtained.

The starting material is manufactured analogously to Example 4 starting from 8 g (28 mmol) of 4-hydroxy-1-[(benzocyclobuten-1-yl)methyl]-1,2,5,6-tetrahydropyridine-3-carboxylic acid ethyl ester and 0.55 g (14 mmol) of sodium borohydride in 160 ml of 50% aqueous ethanol.

EXAMPLE 46

1 g (2.8 mmol) of cis-4-hydroxy-1-[(5-methoxybenzocyclobuten-1-yl)methyl]-piperidine-3-carboxylic acid ethyl ester hydrochloride and 20 ml of 25% aqueous ammonia are stirred for 8 hours with 5 ml of ethanol at 60° C. in a bomb tube. The reaction mixture is then diluted with water and extracted twice with trichloromethane. The extracts are dried over sodium sulphate and concentrated by evaporation. The resulting crude product is dissolved in methanol, titrated to pH 3 with methanesulphonic acid and crystallised by adding diethyl ether. 4-hydroxy-1-[(5-methoxybenzocyclobuten-1-yl)methyl]-piperidine-3-carboxylic acid amide methanesulphonate of m.p. 167°–177° C. is obtained.

EXAMPLE 47

4-hydroxy-1-[(5-chlorobenzocyclobuten-1-yl)methyl]-1,2,5,6-tetrahydro-pyridine-3-carboxylic acid ethyl ester hydrochloride alias 1-[(5-chlorobenzocyclobuten-1-yl)methyl]-4-oxo-piperidine-3-carboxylic acid ethyl ester hydrochloride of m.p. 161°–163° C. can be manufactured analogously to Example 1 from 1 g (20 mmol) of sodium hydride (50% dispersion in mineral oil) and 5.7 g (15.5 mmol) of N-[(5-chlorobenzocyclobuten-1-yl)methyl]imino-di-(3-propionic acid) diethyl ester in 180 ml of toluene.

The starting material, N-[(5-chlorobenzocyclobuten-1-yl)methyl]imino-di-(3-propionic acid) diethyl ester hydrochloride of m.p. 97°–99°, can be manufactured in a manner analogous to that described in Example 1 from 4 g (24 mmol) of 5-chlorobenzocyclobuten-1-ylmethylamine and 7.8 ml (72 mmol) of ethyl acrylate in 80 ml of ethanol.

The required 5-chlorobenzocyclobuten-1-ylmethylamine, m.p. of the hydrochloride 240°–241°, can be manufactured analogously to Example 6 from 5 g (31 mmol) of 5-chlorobenzocyclobutene-1-carboxylic acid nitrile and 4.6 ml (46 mmol) of borane/dimethyl sulphide (10 molar in tetrahydrofuran) in 100 ml of tetrahydrofuran.

EXAMPLE 48

4-hydroxy-1-[(4-methoxybenzocyclobuten-1-yl)methyl]-1,2,5,6-tetrahydro-pyridine-3-carboxylic acid ethyl ester hydrochloride alias 1-[(4-methoxybenzocyclobuten-1-yl)methyl]-4-oxo-piperidine-3-carboxylic acid ethyl ester hydrochloride of m.p. 149°–151° C. can be manufactured analogously to Example 1 from 1.7 g (36 mmol) of sodium hydride (50% dispersion in mineral oil) and 10 g (27 mmol) of N-[(4-methoxybenzocyclobuten-1-yl)methyl]imino-di-(3-propionic acid) diethyl ester in 220 ml of toluene.

The starting material can be manufactured, analogously to Example 1, as follows:

N-[(4-methoxybenzocyclobuten-1-yl)methyl]-]iminodi-(3-propionic acid) diethyl ester is obtained in the form of a viscous oil from 6.2 g (38 mmol) of 4-methoxybenzocyclobuten-1-ylmethylamine and 12 ml (112 mmol) of ethyl acrylate; Rf=0.3, hexane/ethyl acetate (4:1).

The required 4-methoxybenzocyclobuten-1-ylmethylamine, m.p. of the hydrochloride 208°–210°, can be manufactured in a manner analogous to that described in Example 6 from 13 g (80 mmol) of 4-methoxybenzocyclobutene-1-carboxylic acid nitrile and 12 ml (12 mmol) of borane/dimethyl sulphide (10 molar in tetrahydrofuran) in 70 ml of tetrahydrofuran.

EXAMPLE 49

4-hydroxy-1-[(5-methoxy-3-methyl-benzocyclobuten-1-yl)methyl]-1,2,5,6-tetrahydro-pyridine-3-carboxylic acid ethyl ester hydrochloride alias 1-[(5-methoxy-3-methyl-benzocyclobuten-1-yl)methyl]-4-oxo-piperidine-3-carboxylic acid ethyl ester hydrochloride of m.p. 160°–162° can be manufactured analogously to Example 1 from 1.1 g (23 mmol) of sodium hydride (50% dispersion in mineral oil) and 6.6 g (17.5 mmol) of N-[(5-methoxy-3-methyl-benzocyclobuten-1-yl)methyl]-]imino-di-(3-propionic acid) diethyl ester in 230 ml of toluene.

The starting material can be manufactured, analogously to Example 1, as follows:

N-[(5-methoxy-3-methyl-benzocyclobuten-1-yl)methyl]imino-di-(3-propionic acid) diethyl ester is obtained in the form of a viscous oil from 4.1 g (23 mmol) of 5-methoxy-3-methyl-benzocyclobuten-1-ylmethylamine and 7.5 ml (69.5 mmol) of ethyl acrylate; Rf=0.32, hexane/ethyl acetate (4:1).

The starting material can be manufactured analogously to Example 6 by hydrogenating 4.4 g (25 mmol) of 5-methoxy-3-methyl-benzocyclobutene-1-carboxylic acid nitrile with 0.5 g of Raney nickel and 5 g of ammonia in 50 ml of ethanol; m.p. of the hydrochloride 228°–229°.

EXAMPLE 50

4-hydroxy-1-[2-(5-methoxybenzocyclobuten-1-ylidene)ethyl]-1,2,5,6-tetrahydro-pyridine-3-carboxylic acid ethyl ester hydrochloride alias 1-[2-(5-methoxybenzocyclobuten-1-ylidene)ethyl]-4-oxo-piperidine-3-carboxylic acid ethyl ester hydrochloride of m.p. 167°–169° can be manufactured analogously to Example 1 from 110 mg (2.3 mmol) of sodium hydride (50% dispersion in mineral oil) and 580 mg (1.5 mmol) of N-[2-(5-methoxybenzocyclobuten-1-ylidene)ethyl]imino-di-(3-propionic acid) diethyl ester in 60 ml of toluene.

The starting material can be manufactured as follows:

10 g (63 mmol) of 5-methoxybenzocyclobutene-1-carboxylic acid nitrile are introduced at −60° C. under argon into 200 ml of tetrahydrofuran. While stirring, 75 ml (75 mmol) of a 1 molar solution of diisobutyl-aluminium hydride in hexane are slowly added dropwise. The reaction mixture is then allowed to warm slowly to room temperature and is stirred for a further 4 hours. At room temperature, 500 ml of saturated ammonium chloride solution are then added and the whole is subsequently stirred for 40 minutes. 220 ml of 5% sulphuric acid are added and extraction is carried out twice with diethyl ether. The combined organic phases are dried and concentrated. The crude product is purified by chromatography on the ten-fold amount of silica gel. 5-methoxybenzocyclobutene-1-carboxaldehyde, Rf=0.23, hexane/ethyl acetate (9:1), is obtained.

5.5 g (34 mmol) of 5-methoxybenzocyclobutene-1-carboxaldehyde and 13.8 g (42 mmol) of caesium carbonate are introduced under argon into 55 ml of dioxan. While stirring, 8.7 g (39 mmol) of phosphonoacetic acid triethyl ester are added and the whole is then heated at 80° for 2 hours. The reaction mixture is then concentrated, taken up in dichloromethane and washed with water. The organic phase is dried over sodium sulphate and concentrated by evaporation. The crude product so obtained is purified by chromatography on silica gel. 3-(5-methoxybenzocyclobuten-1-yl)acrylic acid ethyl ester is obtained; Rf=0.5, hexane/diethyl ether (4:1).

7.3 g (31.5 mmol) of 3-(5-methoxybenzocyclobuten-1-yl)acrylic acid ethyl ester are stirred in 140 ml of 50% aqueous ethanol with 7 g (125 mmol) of potassium hydroxide for 5 hours at 50°. The reaction mixture is then adjusted to pH 1 with concentrated hydrochloric acid and extracted three times with dichloromethane. The combined organic extracts are dried over sodium sulphate and concentrated by evaporation. The crude product is purified by chromatography on silica gel and then crystallised from diethyl ether/hexane. There is thus obtained 3-(5-methoxybenzocyclobuten-1-ylidene)propionic acid of m.p. 134°–137°.

2.1 g (10 mmol) of 3-(5-methoxybenzocyclobuten-1-ylidene)propionic acid and 1.4 ml (10 mmol) of triethylamine are introduced under argon into 20 ml of toluene. 2.2 ml (10 mmol) of diphenylphosphorylazide are added thereto and the whole is heated, while stirring, at 80° for 30 minutes. The mixture is allowed to cool to room temperature, 2.9 ml (20 mmol) of 2-trimethyl- silylethanol are added thereto and the whole is heated at 80° for 7 hours. The reaction mixture is then concentrated to dryness in a rotary evaporator. The oily residue is taken up in diethyl ether, washed with water and 2N sodium hydroxide solution, dried over sodium sulphate and concentrated by evaporation. The crude product is purified by chromatography on a silica gel column, stirred at 50° for 2 hours with 10 ml (10 mmol) of a 1 molar solution of tetrabutylammonium fluoride in tetrahydrofuran and then concentrated to dryness by evaporation. The residue is stirred vigorously with n-pentane/water (1:1). The n-pentane phase is separated off and discarded. The aqueous phase is adjusted to pH 8 with ammonium chloride, whereupon a crystalline product precipitates. The latter is filtered off with suction. The mother liquor is saturated with sodium chloride, whereupon more product crystallises out. The crystallisates are combined, taken up in trichloromethane/methanol (1:1), dried over sodium sulphate and concentrated by evaporation. The crystalline residue is stirred with diethyl ether and then filtered. 2-(5-methoxybenzocyclobuten-1-ylidene)ethylamine of m.p. 238°–240° is obtained.

580 mg (3.3 mmol) of 2-(5-methoxybenzocyclobuten-1-ylidene)ethylamine are reacted, in a manner analogous to that described in Example 1, in 20 ml of ethanol with 1.1 ml (9.9 mmol) of ethyl acrylate to form N-[2-(5-methoxybenzocyclobuten-1-ylidene)ethyl]imino-di-(3-propionic acid) diethyl ester; Rf=0.14, hexane/ethyl acetate (4:1).

EXAMPLE 51

4-hydroxy-1-[(6-methoxyindan-2-yl)methyl]-1,2,5,6-tetrahydro-pyridine-alias 1-[(6-methoxyindan-2-yl)methyl]-4-oxo-piperidine-3-carboxylic acid ethyl ester and the hydrochlorides thereof is obtained in a manner analogous to that described in Example 1 from N-(6-methoxyindan-2-yl)methyl]imino-di-(3-propionic acid) diethyl ester.

The starting material can be obtained, for example, starting from 6-methoxyindan-1-one by α-metallation and reaction with chloroformic acid methyl ester to form 6-methoxy-1-oxo-indane-2-carboxylic acid methyl ester, hydrogenation of the latter to 6-methoxyindane-2-carboxylic acid methyl ester, reduction with lithium aluminium hydride to 6-methoxyindane-2-methanol, conversion of the latter by means of methanesulphonic acid chloride/sodium azide and reduction again with lithium aluminium hydride and reaction of the resulting 6-methoxyindan-2-ylmethylamine with double the molar amount of ethyl acrylate.

EXAMPLE 52

1-[(6-methoxyindan-2-yl)methyl]-1,2,5,6-tetrahydro-pyridine-3-carboxylic acid methyl ester and its hydrochloride (melting point: 160°–162°) are obtained in a manner analogous to that described in Example 30 by reacting methanesulphonic acid (6-methoxyindan-2-ylmethyl) ester, obtainable from 6-methoxyindane-2-methanol (cf. Example 51), with guvacoline hydrobromide and N-ethyl-N,N-diisopropylamine.

EXAMPLE 53

In a manner analogous to that described in Example 1, there is obtained from 6-methoxyindan-2-ylamine, obtainable from 6-methoxyindane-2-carboxylic acid methyl ester via 6-methoxyindane-2-carboxylic acid azide and Curtins degradation, and methyl acrylate, 4-hydroxy-1-(6-methoxyindan-2-yl)-1,2,5,6-tetrahydropyridine- alias 1-(6-methoxyindan-1-yl)-4-oxo-piperidine-3-carboxylic acid methyl ester and its hydrochloride (melting point: 166°–168°), and, from the latter, in a manner analogous to that described in Examples 28 and 29, 1-(6-methoxyindan-2-yl)-1,2,5,6-tetrahydro-pyridine-3-carboxylic acid methyl ester and its hydrochloride.

EXAMPLE 54

By catalytic hydrogenation of 1-[(5-methoxybenzocyclobuten-1-yl)methyl]-1,2,5,6-tetrahydro-pyridine-3-carboxylic acid ethyl ester there is obtained 1-[(5-methoxybenzocyclobuten-1-yl)methyl]-piperidine-3-carboxylic acid ethyl ester and, by hydrolysis thereof, 1-[(5-methoxybenzocyclobuten-1-yl)methyl]-piperidine-3-carboxylic acid and also the respective hydrochlorides thereof.

EXAMPLE 55

To a solution of 7.27 g (30 mmol) of methanesulphonic acid (5-methoxybenzocyclobuten-1-yl)methyl ester in 60 ml of dimethylformamide there are added first 5.66 g (36 mmol) of piperidine-3-carboxylic acid ethyl ester and then 9.70 g (75 mmol) of N-ethyl-N,N-diisopropylamine. The mixture is stirred at 60° for 18 hours and, after cooling, is concentrated by evaporation under a high vacuum. The residue is taken up in diethyl ether and washed with water, and the organic phase is extracted with 2N hydrochloric acid. The hydrochloric acid extracts are combined, rendered alkaline at reduced temperature with concentrated sodium hydroxide solution and extracted with dichloromethane. The combined organic phases are dried over sodium sulphate and concentrated to dryness by evaporation under reduced pressure. 1-[(5-methoxybenzocyclobuten-1-yl)methyl]-piperidine-3-carboxylic acid ethyl ester is obtained in the form of a yellow oil.

The hydrochloride produced with hydrochloric acid in diethyl ether crystallises from ethanol/diethyl ether with m.p. 193°–195° (decomposition).

EXAMPLE 56

31.5 ml (31.5 mmol) of N sodium hydroxide solution are added to a solution of 5.10 g (15 mmol) of 1-[(5-methoxybenzocyclobuten-1-yl)methyl]piperidine-3-carboxylic acid ethyl ester hydrochloride in 60 ml of ethanol. After stirring for 5 minutes at room temperature, 40 ml of water are added, and the mixture is heated to 50°–60° and maintained at that temperature for 30 minutes. After cooling, 15 ml of concentrated hydrochloric acid are added to the solution and the whole is concentrated by evaporation under reduced pressure. The residue is taken up in 150 ml of hot acetone and the insoluble sodium chloride is separated off. After concentrating the acetone solution to 50 ml, 1-[(5-methoxybenzocyclobuten-1-yl)methyl]piperidine-3-carboxylic acid hydrochloride of m.p. 195°–198° crystallises out.

EXAMPLE 57

In a manner analogous to that described in Examples 13 and 27, by reacting
2-(5-methoxybenzocyclobuten-1-yl)ethylamine,
6-methoxyindan-1-ylmethylamine,
2-(6-methoxyindan-1-yl)ethylamine,
6-methoxyindan-1-ylamine,
7-methoxy-1,2,3,4-tetrahydro-naphth-1-ylmethylamine,
5-hydroxybenzocyclobuten-1-ylmethylamine, benzocyclobuten-1-ylmethylamine,
5-chlorobenzocyclobuten-1-ylmethylamine,
4-methoxybenzocyclobuten-1-ylmethylamine,
5-methoxy-3-methyl-benzocyclobuten-1-ylmethylamine,
5-methoxy-1-methyl-benzocyclobuten-1-ylmethylamine,
2-(5-methoxybenzocyclobuten-1-ylidene)ethylamine and
6-methoxyindan-2-ylmethylamine with the equimolar amount in each case of ethyl acrylate in ethanolic solution there are obtained
3-[2-(5-methoxybenzocyclobuten-1-yl)ethylamino]propionic acid ethyl ester,
3-(6-methoxyindan-1-ylmethylamino)propionic acid ethyl ester,
3-[2-(6-methoxyindan-1-yl)ethylamino]propionic acid ethyl ester,
3-(6-methoxyindan-1-ylamino)propionic acid ethyl ester,
3-(7-methoxy-1,2,3,4-tetrahydro-naphth-1-ylmethylamino)propionic acid ethyl ester,
3-(5-hydroxybenzocyclobuten-1-ylmethylamino)propionic acid ethyl ester,
3-(benzocyclobuten-1-ylmethylamino)propionic acid ethyl ester,
3-(5-chlorobenzocyclobuten-1-ylmethylamino)propionic acid ethyl ester,
3-(4-methoxybenzocyclobuten-1-ylmethylamino)propionic acid ethyl ester,
3-(5-methoxy-3-methyl-benzocyclobuten-1-ylmethylamino)propionic acid ethyl ester,
3-(5-methoxy-1-methyl-benzocyclobuten-1-ylmethylamino)propionic acid ethyl ester,
3-[2-(5-methoxybenzocyclobuten-1-ylidene)ethylamino]propionic acid ethyl ester and
3-(6-methoxyindan-2-ylmethylamino)propionic acid ethyl ester, and by hydrolysis of
3-(6-methoxybenzocyclobuten-1-ylmethylamino)propionic acid ethyl ester in a manner analogous to that described in Example 56
3-(6-methoxybenzocyclobuten-1-ylmethylamino)propionic acid and the respective acid addition salts, for example hydrochlorides, thereof.

EXAMPLE 58

In a manner analogous to that described in Examples 13 and 26, by reacting
5-methoxybenzocyclobuten-1-ylmethylamine,
2-(5-methoxybenzocyclobuten-1-yl)ethylamine,
2-(indan-1-yl)ethylamine,
6-methoxyindan-1-ylmethylamine,
2-(6-methoxyindan-1-yl)ethylamine,
7-methoxy-1,2,3,4-tetrahydro-naphth-2-ylmethylamine and
6-methoxyindan-2-ylmethylamine with the equimolar amount in each case of methyl acrylate there are obtained
3-(5-methoxybenzocyclobuten-1-ylamino)propionic acid methyl ester,
3-[2-(5-methoxybenzocyclobuten-1-yl)ethylamino]propionic acid methyl ester,
3-(2-indan-1-ylethylamino)propionic acid methyl ester,
3-(6-methoxyindan-1-ylmethylamino)propionic acid methyl ester,
3-[2-(6-methoxyindan-1-yl)ethylamino]propionic acid methyl ester,
3-(7-methoxyindan-1-ylmethylamino]propionic acid methyl ester and
3-(6-methoxyindan-2-ylmethylamino)propionic acid methyl ester
and the acid addition salts, for example hydrochlorides, thereof.

EXAMPLE 59

Tablets, each containing 25 mg of active ingredient, for example 4-hydroxy-1-[(5-methoxybenzocyclobuten-1-yl)methyl]-1,2,5,6-tetrahydro-pyridine-3-carboxylic acid ethyl ester hydrochloride alias 1-[(5-methoxybenzocyclobuten-1-yl)methyl]-4-oxo-piperidine-3-carboxylic acid ethyl ester hydrochloride, can be manufactured in the following manner:

| Composition (for 1000 tablets) | |
|---|---|
| active ingredient | 25.0 g |
| lactose | 100.7 g |
| wheat starch | 7.5 g |
| polyethylene glycol 6000 | 5.0 g |
| talcum | 5.0 g |
| magnesium stearate | 1.8 g |
| demineralised water | q.s. |

Manufacture

All the solid ingredients are first forced through a sieve of 0.6 mm mesh width The active ingredient, the lactose, the talcum, the magnesium stearate and half of the starch are then mixed together. The other half of the starch is suspended in 40 ml of water and this suspension is added to a boiling solution of the polyethylene glycol in 100 ml of water. The resulting starch paste is added to the main batch and the mixture is granulated, if necessary with water being added. The granulate is dried overnight at 35°, forced through a sieve of 1.2 mm mesh width and compressed to form tablets of approximately 6 mm diameter which are concave on both sides.

EXAMPLE 60

Tablets, each containing 50 mg of the active ingredient, for example 4-hydroxy-1-[(5-methoxybenzocyclobuten-1-yl)methyl]-1,2,5,6-tetrahydro-pyridine-3-carboxylic acid ethyl ester hydrochloride alias 1-[(5-methoxybenzocyclobuten-1-yl)methyl]-4-oxo-piperidine-3-carboxylic acid ethyl ester hydrochloride, can be manufactured as follows:

| Composition (for 10,000 tablets) | |
|---|---|
| active ingredient | 500.00 g |
| lactose | 140.80 g |
| potato starch | 274.70 g |
| stearic acid | 10.00 g |
| talc | 50.00 g |
| magnesium stearate | 2.50 g |
| colloidal silica | 32.00 g |
| ethanol | q.s. |

A mixture of the active ingredient, the lactose and 194.70 g of potato starch is moistened with an ethanolic solution of the stearic acid and the whole is granulated through a sieve. After drying, the remainder of the potato starch, the talc, the magnesium stearate and the colloidal silica are mixed in and the mixture is compressed to form tablets each weighing 0.1 g which may, if desired, be provided with dividing notches for finer adaptation of the dosage.

100 mg of active ingredient can be incorporated in an analogous manner.

EXAMPLE 61

Capsules, each containing 0.025 g of the active ingredient, for example 4-hydroxy-1-[(5-methoxybenzocyclobuten-1-yl)methyl]-1,2,5,6-tetrahydro-pyridine-3-carboxylic acid ethyl ester hydrochloride alias 1-[(5-methoxybenzocyclobuten-1-yl)methyl]-4-oxo-piperidine-3-carboxylic acid ethyl ester hydrochloride, can be manufactured as follows:

| Composition: (for 1000 capsules) | |
|---|---|
| active ingredient | 25.00 g |
| lactose | 249.00 g |
| gelatine | 2.00 g |
| corn starch | 10.00 g |
| talc | 15.00 g |
| water | q.s. |

The active ingredient is mixed with the lactose, the mixture is moistened uniformly with an aqueous solution of the gelatine and the whole is granulated though a sieve of mesh width 1.2 to 1.5 mm. The granulate is mixed with the dried corn starch and the talc and the mixture is introduced into hard gelatine capsules (size 1) in portions of 300 mg.

In a manner analogous to that described in Examples 59-61 it is also possible to manufacture pharmaceutical preparations containing a different compound of the formula I, for example one according to Examples 1 to 56, or a compound of the formula IVc, for example according to Example 57.

We claim:

1. A hydropyridine derivative of the formula

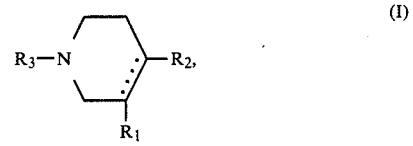

in which $R_1$ represents carboxy, lower alkoxycarbonyl, carbamoyl, N-lower alkylcarbamoyl or N,N-di-lower alkylcarbamoyl, $R_2$ represents hydrogen hydroxy, lower alkoxy, phenyl-lower alkoxy which is unsubstituted or substituted, substituents being selected from the group consisting of lower alkyl, lower alkoxy and halogen, lower alkanoyloxy, benzoyloxy, puridoyloxy, lower alkanesulphonyloxy, lower alkoxycarbonyloxy, phenyl-lower alkoxycarbonyloxy, amino, lower alkoxyolamino, benzoylamino, pyridoylamino, lower alkanesulphonylamino, lower alkoxycarbonylamino or phenyl-lower alkoxycarbonylamino, $R_3$ represents a radical of the formula R—(Ia), R-alk$_1$- (Ib) or R'=alk2- (Ic), in which R represents a benzocycloalkenyl radical having a total of from 8 to 12 ring carbon atoms and which is bonded via a saturated carbon atom, said benzoycloakenyl moiety being unsubstituted or mono- or poly-substituted in the benzo moiety, substituents being selected from the group consisting of hydroxy, lower alkoxy, lower alkanoyloxy, halogen, lower alkyl and trifluoromethyl, and the alpha-carbon atom of said R next to the benzo portion being unsubstituted or substituted by lower alkyl, R' represents a benzocycloalkylidene radical having a total of from 8 to 12 ring carbon atoms, said benzocycloalkenylidene moiety being unsubstituted or mono- or poly-substituted in the benzo moiety, substituents being selected from the group consisting of hydroxy, lower alkoxy, lower alkanoyloxy, halogen, lower alkyl and trifluoromethyl, alk$_2$ represents lower alkylene or lower alkylidene and alk$_2$ represents lower alkyl-ω-ylidene, and the dotted line is intended to show that there may be a single bond or a double bond between the carbon atoms carrying the substituents $R_1$ and $R_2$, or a tautomer thereof, in each case in free form or in form of a salt.

2. A compound according to claim 1, in which $R_3$ is a group Ia, Ib or Ic, R represents a benzocyclobuten-1-yl radicals, indan-1-yl or indan-2-yl radical or 1,2,3,4-tetrahydronaphth-1-yl or 1,2,3,4-tetrahydronaphth-2-yl radical each of which is unsubstituted or is mono- or poly-substituted in the benzo moiety, substituents being selected from the group consisting of hydroxy, lower alkoxy, lower alkanyloxy and halogen, and the alpha-carbon atom of said R next to the benzo portion being unsubstituted or substituted by lower alkyl, $R^1$ is a benzocyclobuten-1-ylidene radical which is unsubstituted or is mono- or polysubstituted in the benzo moiety, substituents being selected from the group consisting of hydroxy, lower alkoxy, lower alkanoyloxy and halogen, $R_1$ represents carboxy, lower alkoxycarbonyl or carbamoyl $R_2$, represents hydrogen, hydroxy, lower alkoxy, lower alkanoyloxy, lower alkanesulphonyloxy, phenyl-lower alkoxy which is unsubstituted or substituted in the phenyl moiety, substituents being selected from the group consisting of lower alkyl, lower alkoxy and halogen, or amino, $alk_1$ represents lower alkylene which connects the two ring systems by 1 up to and including 3 carbon atoms or lower alkylidene, $alk_2$ represents lower alkyl-ω-ylidene which connects the two ring systems by 2 or 3 carbon atoms and the dotted line is intended to show that these may be a single bond or a double bond, or a tautomer thereof, in each case in free form or in the form of a salt.

3. A compound according to claim 1, in which $R_3$ represents a group Ia or Ib, R represents a benzocyclobuten-1-yl radical, indan-1-yl, indan-2-yl or 1,2,3,4-tetrahydronaphth-1-yl radical each of which is unsubstituted or is mono-substituted in the benzo moiety by lower alkoxy having up to and including 4 carbon atoms, lower alkyl having up to and including 4 carbon atoms or by fluorine, chlorine or bromine or is di-substituted in the benzo moiety by lower alkyl having up to and including 4 carbon atoms or by lower alkoxy having up to and including 4 carbon atoms, $R_1$ represents lower alkoxycarbonyl having from 2 up to and including 5 carbon atoms or carbamoyl, $R_2$ represents hydrogen or hydroxy, $alk_1$ represents lower alkylene which bridges the two ring systems by from 1 up to and including 3 carbon atoms and has up to and including 3 carbon atoms and the dotted line is intended to show that there may be a single bond or a double bond, or a tautomer thereof, in each case in free form or in form of a salt.

4. A compound according to claim 1, in which $R_3$ represents a group of the formula Ib, R represents a benzocyclobuten-1-yl radical which is unsubstituted or is mono-substituted in the benzo moiety by lower alkoxy having up to and including 4 carbon atoms, $R_1$ represents carboxy, lower aloxycarbonyl having from 2 up to and including 5 carbon atoms or carbamoyl, $R_2$ represents hydrogen or hydroxyl, $alk_1$ represents lower alkylene which bridges the two ring systems by from 1 up to and including 3 carbon atoms and has up to and including 3 carbon atoms and the dotted line is intended to show that there may be a single bond or a double bond, or a tautomer thereof, in each case in free form or in form of a salt.

5. A compound according to claim 1, in which $R_3$ represents a group of the formula Ib, R represents a benzocyclobutene-1-yl radical which is unsubstituted or is mono-substituted in the benzo moiety by lower alkoxy having up to and including 4 carbon atoms, $R_1$ represents lower alkoxycarbonyl having from 2 up to and including 5 carbon atoms, $R_2$ represents hydroxy, $alk_1$ represents methylene or ethylene, and the dotted line is intended to show that there may be a single bond or a double bond, or a tautomer thereof, in each case in free form of a salt.

6. A compound according to claim 1 being 4-hydroxy-1-[(5-methoxybenzocyclobuten-1-yl)methyl]-1,2,5,6-tetrahydrophyridine-3-carboxylic acid ethyl ester or 1-[(5-methoxybenzocyclobuten-1-yl)methyl]-4-oxo-piperidine-3-carboxylic acid ethyl ester, or in each case a salt thereof.

7. A compound according to claim 1 being 4-hydroxy-1-[(5-methoxybenzocyclobuten-1-yl)methyl]-1,2,5,6-tetrahydrophyridine-3-carboxylic acid ethyl ester or 1-[(5-methoxybenzocyclobuten-1-yl)methyl]-4-oxo-piperidine-3carboxylic acid methyl ester, or in each case a salt thereof.

8. A compound according to claim 1 being cis-4-hydroxy-1-[(5-methoxybenzocyclobuten-1-yl)methyl]-piperidine-3-carboxylic acid ethyl ester or salt thereof.

9. A compound according to claim 1 being trans-4-hydroxy-1-[(5-methoxybenzocyclobuten-1-yl)methyl]-piperidine-3-carboxylic acid ethyl ester or a salt thereof.

10. A compound according to claim 1 being 1-[(5-methoxybenzocyclobuten-1-yl)methyl]-1,2,5,6-tetrahydro-pyridine-3-carboxylic ethyl ester or a salt thereof.

11. A compound according to claim 1 being 4-hydroxy-1-[(6-methoxyindan-1-yl)methyl]-1,2,5,6-tetrahydro-pyridine-3-carboxylic ethyl ester or 1-[(6-methoxyindan-1-yl)methyl]-4-oxo-piperidine-3-carboxylic acid ethyl ester, or in each case a salt thereof.

12. A pharmaceutical composition comprising as the active ingredient a therapeutically effective amount of a compound according to claim 1, in free form or in form of a pharmaceutically acceptable salt, together with pharmaceutically acceptable adjuncts.

13. A method of treatment of symptoms of cerebral insufficiency, characterized in that a therapeutically effective amount of a compound according to claim 1, in free form or in form of a pharmaceutically acceptable salt, is administered to a subject in need of such treatment.

* * * * *